United States Patent [19]

Schirlin et al.

[11] Patent Number: 5,693,668
[45] Date of Patent: Dec. 2, 1997

[54] ACETYLCHOLINESTERASE INHIBITORS

[75] Inventors: Daniel Schirlin, Lampertheim; Jean-Noël Collard, Illkirch Graffenstaden; Jean-Marie Hornsperger, Griesheim-prés-Molsheim, all of France; Prakash R. Keshary, Overland Park, Kans.

[73] Assignee: Merrell Pharmaceuticals Inc., Cincinnati, Ohio

[21] Appl. No.: 382,941

[22] Filed: Jan. 31, 1995

Related U.S. Application Data

[63] Continuation of Ser. No. 210,800, Mar. 18, 1994, abandoned, which is a continuation-in-part of Ser. No. 32,564, Mar. 17, 1993, abandoned, which is a continuation of Ser. No. 878,576, May 5, 1992, abandoned, which is a continuation-in-part of Ser. No. 629,541, Dec. 18, 1990, abandoned, which is a continuation-in-part of Ser. No. 542,285, Jun. 22, 1990, abandoned.

[30] Foreign Application Priority Data

Jun. 22, 1989 [EP] European Pat. Off. .............. 89401775
Jun. 20, 1990 [EP] European Pat. Off. .............. 90401475

[51] Int. Cl.$^6$ .............................. A61K 31/28; C07F 7/04
[52] U.S. Cl. .......................... 514/492; 556/436; 556/441
[58] Field of Search ........................... 514/492; 556/436, 556/441

[56] References Cited

U.S. PATENT DOCUMENTS

| | | | |
|---|---|---|---|
| 3,651,115 | 3/1972 | Belsky et al. | 260/448.2 N |
| 4,835,099 | 5/1989 | Mize et al. | 435/7 |
| 4,914,221 | 4/1990 | Winkler et al. | 556/436 |
| 5,008,425 | 4/1991 | Stahly | 556/436 |

OTHER PUBLICATIONS

Gelb et al., Biochemistry, vol. 24, No. 8, pp. 1813–1817 (1985).
U. Brodbeck et al., Biochimica et Biophysica Acta, 567, pp. 357–369 (1979).
K. N. Allen et al., Biochemistry 28, pp. 8466–8473 (1989).
H.K. Nair, et al., J. Am. Chem. Soc., 115, pp 9939–9941 (1993).
R.L. Metcalf et al., J. Econ. Entomol. 58, p. 1151 (1965).
A. Aberman et al., Biochimica et Biophysica Acta, 791, pp. 278–280 (1984).
R.L. Salvador et al., Tetrahedron. vol. 27, pp. 1221–1226 (1971).

*Primary Examiner*—Porfirio Nazario-Gonzalez
*Attorney, Agent, or Firm*—Stephen L. Nesbitt; Barbara E. Kurys

[57] ABSTRACT

This invention relates to silylated aromatic fluoroketones possessing acetylcholinesterase-inhibiting properties and to their use in the treatment of Alzheimer disease and senile dementia.

21 Claims, No Drawings

ACETYLCHOLINESTERASE INHIBITORS

This is a continuation of application Ser. No. 08/210,800, filed Mar. 18, 1994, now abandoned, which is a continuation-in-part of application Ser. No. 08/032,564, filed Mar. 17, 1993, now abandoned, which is a continuation of application Ser. No. 07/878,576, filed May 5, 1992, now abandoned, which is a continuation-in-part of application Ser. No. 07/629,541, filed Dec. 18, 1990, now abandoned, which is a continuation-in-part of application Ser. No. 07/542,285, flied Jun. 22, 1990, now abandoned, which are herein incorporated by reference.

This invention relates to silylated aromatic fluoroketones, formylketones, and pentafluoroethyl ketones, to the intermediates and processes for their preparation and to their use in treating diseases associated with deficiencies of cholinergic transmission in the central nervous system.

More specifically, this invention relates to silylated aromatic fluoroketones, formylketones, and pentafluoroethyl ketones possessing acetylcholinesterase-inhibiting properties and to their use in the treatment of Alzheimer disease and senile dementia.

Still more specifically, this invention relates to acetylcholinesterase inhibitors of the formula

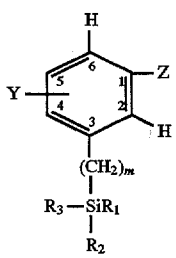

and the pharmaceutically acceptable salts thereof, wherein Z is —C(O)C(O)R', —C(O)CF$_2$CF$_3$, or —(CH$_2$)$_n$—Q—CF$_2$X, each of m and n is zero or one with the proviso that the sum of m and n is less than two,

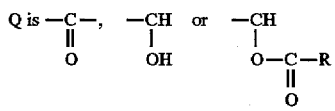

with R being H or C$_{1-10}$ alkyl
X is X' or X" with

X' being H, Br, Cl, F or R$_4$ and
X" being COR$_9$, CO$_2$R$_5$, CONHR$_5$ or COR$_6$, R$_1$, R$_2$, R$_3$ and R$_4$ each are C$_{1-10}$ alkyl, or (CH$_2$)$_p$ aryl, with p being zero, one or two, R' and R$_5$ are H, C$_{1-10}$ alkyl, phenyl, benzyl or phenethyl,
R$_9$ is C$_{1-10}$ alkyl, phenyl, benzyl or phenethyl, R$_6$ is (NHCHR$_7$C(O))$_q$R$_8$ with R$_7$ being the residue of any natural occurring α-amino acid, q is one to four and R$_8$ is OR$_5$ or NHR$_5$, Y is H, OH, C$_{1-6}$ alkyl, C$_{1-6}$ alkoxy, hydroxy C$_{1-6}$ alkyl, amino C$_{1-6}$ alkyl, NH$_2$, azido, CN, CO$_2$R$_5$, COR$_9$, —SO$_3$H, Br, Cl, F or —(CH$_2$)$_x$SiR$_1$R$_2$R$_3$ with x being zero, one or two.

As used herein the term "alkyl" includes the straight, branched-chain and cyclized saturated hydrocarbyl moieties having up to 10 (or 6 as otherwise indicated) particularly including such moieties as methyl, ethyl, n-butyl, t-butyl, cyclopropyl, n-propyl, pentyl, hexyl, n-nonyl, decyl, cyclopentyl, cyclohexyl and cyclohexylmethylene. The term "aryl" within the definitions for R$_1$, R$_2$, R$_3$ and R$_4$ includes both carbocyclic and heterocyclic moieties of which phenyl, pyridyl, indolyl, indazolyl, furyl and thienyl are of primary interest; these moieties being inclusive of their position isomers such as, for example, 2-, 3-, or 4-pyridyl, 2- or 3-furyl and thienyl, 1-, 2-, or 3-indolyl or the 1- and 3-indazolyl, as well as the dihydro and tetrahydro analogs of the furyl and thienyl moieties. Also included within the term "aryl" are such fused carbocyclic moieties as pentalenyl, indenyl, naphthalenyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl and naphthacenyl. Also included within the term "aryl" are such other heterocyclic radicals as 2- or 3-benzo[b]thienyl, 2-or3-naphtho[2,3-b]thienyl, 2- or 3-thianthrenyl, 2H-pyran-3-(or 4- or 5-)yl, 1-isobenzofuranyl, 2H-chromenyl-3-yl, 2- or 3-xanthenyl, 2- or 3-phenoxathiinyl, 2- or 3-pyrrolyl, 4- or 3-pyrazolyl, 2-pyrazinyl, 2-pyrimidinyl, 3-pyridazinyl, 2-pyrimidinyl, 3-pyridazinyl, 2-indolizinyl, 1-isoindolyl, 4H-quinolizin-2-yl, 3-isoquinolyl, 2-quinolyl, 1-phthalazinyl, 1,8-naphthyridinyl, 2-quinoxalinyl, 2-quinazolinyl, 3-cinnolinyl, 2-pteridinyl, 4aH-carbazol-2-yl, 2-carbazolyl, β-carbolin-3-yl, 3-phenanthridinyl, 2-acridinyl, 2-perimidinyl, 1-phenazinyl, 3-isothiazolyl, 2-phenothiazinyl, 3-isoxazolyl, 2-phenoxazinyl, 3-isochromanyl, 7-chromanyl, 2-pyrrolidinyl, 2-pyrrolin-3-yl, 2-imidazolidinyl, 2-imidazolin-4-yl, 2-pyrazolidinyl, 3-pyrazolin-3-yl, 2-piperidyl, 2-piperazinyl, 1-indolinyl, 1-isoindolinyl, 3-morpholinyl, benzo[h]isoquinolinyl, and benzo[b]furanyl, including the position isomers thereof except that the heterocyclic moieties cannot be attached directly through their nitrogen atoms.

The term [NHCHR$_7$C(O)]$_q$ of R$_6$ represents an α-amino acid or a peptide of up to 4 amino acids, with R$_7$ being the residue of any of the naturally occurring α-amino acids (including proline in its natural form) including alanine, arginine, asparagine, aspartic acid, cysteine, glutamine, glutamic acid, glycine, histidine, isoleucine, leucine, lysine, methionine, phenylalanine, serine, threonine, tryptophan, tyrosine, valine, nor-valine, n-leucine, 1-naphthylalanine, 2-indolinecarboxylic acid and sarcosin. Of course when q is other than 1 the amino acid moieties may be the same or different. Preferably R$_8$ represents either OH or NH$_2$ but includes the R$_5$ variants thereof, particularly when R$_5$ is methyl or ethyl.

The pharmaceutically acceptable salts of the compounds of formula I include salts formed with non-toxic organic or inorganic acids such as, for example, from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The preparation of the compounds of formula I may be effected by a variety of procedures, the choice depending upon the specific combination of the X, Y, m, n, R$_1$, R$_2$ and R$_3$ moieties for any given compound. In any event, the chemical reactions and procedures are analogously known in the art and the selection of any particular route to prepare any particular compound is governed by principles well known and appreciated by those of ordinary skill in the art. Thus, by the application of the below-described procedures and chemical processes generally well-known in the art, the compounds of this invention may be prepared. To prepare compounds of subgeneric formula

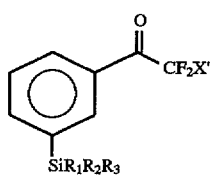

i.e., those compounds of formula I wherein m and n are zero,
Y is H, and

X' is H, Cl, Br, F or $R_4$, the compounds may be prepared by the following reaction scheme.

Reaction Scheme A

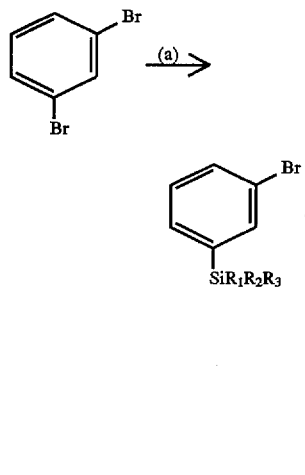

wherein $R_1$, $R_2$, $R_3$ and $R_4$ are as defined in formula I, and X' is H, Cl, Br, F or $R_4$. In the initial step (A-a) the reaction involves the treatment of the dibromo compounds (A-11) with $ClSiR_1R_2R_3$ in the presence of one equivalent of magnesium in a suitable solvent such as diethylether or tetrahydrofuran (THF), said reaction taking place at about the reflux temperature of the mixture to obtain the silylated derivatives (A-12) which, by Step (A-b), are converted to their intermediate lithio derivatives by reaction with an alkyllithium at 0° C. in diethyl ether or THF and those intermediates are converted to the desired products (A-13) by reaction with three equivalents of the appropriate acid, (preferably as its lithium salt) ester (X'CF$_2$CO$_2$R), or acid chloride (X'CF$_2$COCl) with R being H or $C_{1-6}$ alkyl, preferably methyl or ethyl). The ketones may be reduced with sodium borohydride or sodium cyano borohydride by reaction in ethanol followed by hydrolysis with saturated ammonium chloride and the resulting alcohols esterified with an acyl halide (ClC(O)R with R being H or $C_{1-10}$ alkyl), in the presence of TEA (or neat pyridine) in a suitable solvent such as dichloromethane; both these reactions being effected according to well known and understood reaction conditions.

In those instances wherein it is desired to prepare compounds of this invention which are within the sub-generic scope of the formula

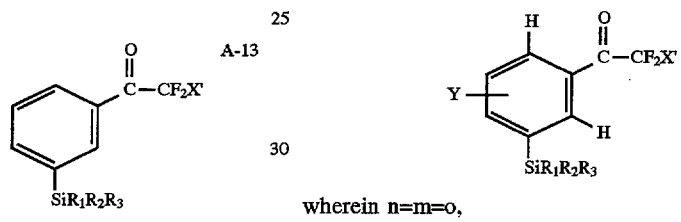

wherein n=m=o,

Y is other than H, and

X' is H, Br, Cl, F or $R_4$, the chemistry of the following reaction scheme may be utilized.

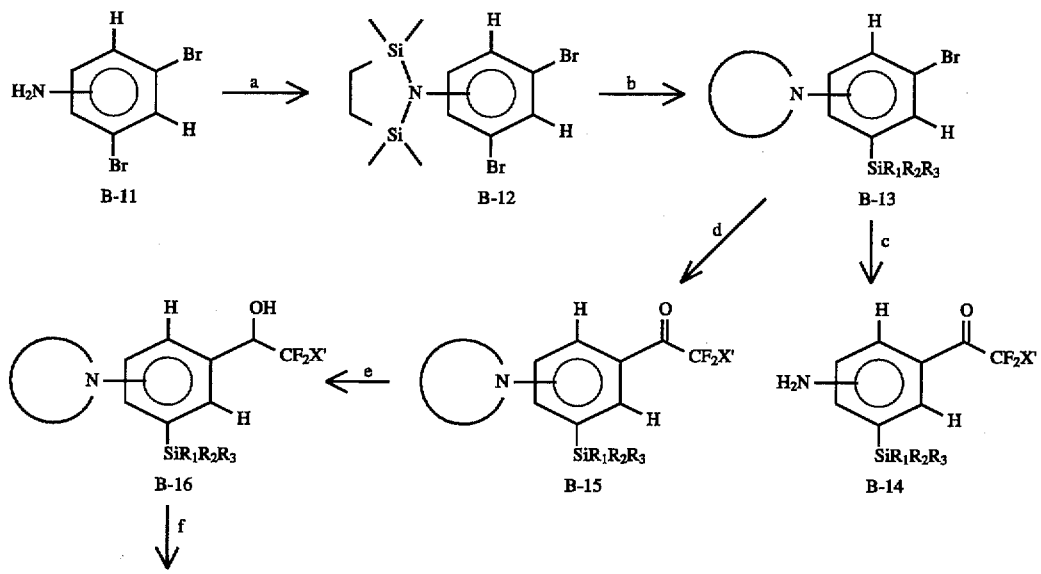

-continued
Reaction Scheme B

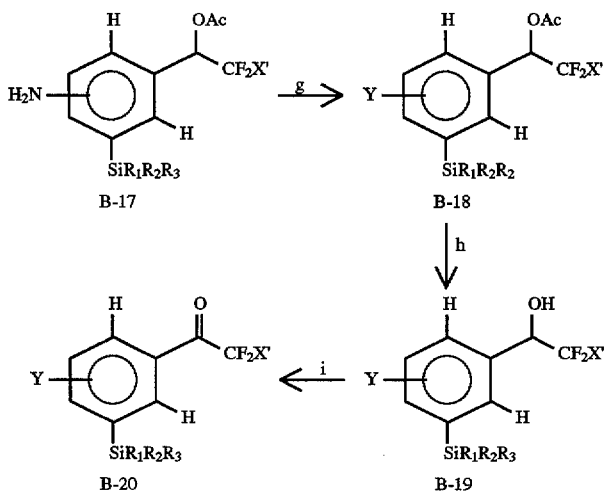

Again, in effecting the foregoing reactions, standard procedures analogously known in the art are employed. Step (B-a) entails the treatment of the amines (B-11) with one equivalent of butyl lithium in THF at about −30° C. to form an in situ intermediate which is reacted with one equivalent of 1,4-dichloro-1,1,4,4-tetramethyldisilylethylene at about −78° C. The stabase adduct intermediates (B-12) are subjected to Step (B-b) using the silylation process of Step (A-a) and the resulting products (B-13) by Step (B-c) are sequentially converted to their lithio derivatives by reaction with butyl lithium in diethylether at 0° C. for 15 minutes and these lithio derivatives are reacted with 3 equivalents of an acid, ester (X'CF$_2$CO$_2$R) or a lithio salt thereof, or acid chloride (X'CF$_2$COCl) at −78° C. to obtain products (B-14). Alternatively using Step (B-d), which in principle follows Step (B-c), except that the hydrolysis is performed preferably using an aqueous ammonium chloride solution to produce compounds (A-15). Step (B-e) reduces the ketones of (B-15), preferably using sodium cyanoborohydride in ethanol followed by hydrolysis with a saturated aqueous ammonium chloride solution to produce the alcohols of (B-16). Using Step (B-f) the alcohols are protected by reaction with an acyl halide, preferably acetyl chloride, in the presence of triethylamine (TEA) in a solvent such as dichloromethane followed by an acid hydrolysis, preferably using 1N HCl to convert the stabase adduct to an amine (in the form of an ammonium salt) to obtain products (B-17). Step (B-g) involves a multiplicity of reactions which essentially are designed to effect Y-substitution on the phenyl ring of the involved compounds of (B-17). In general, these reactions involve the conversion of the ammonium salt to a diazonium salt (e.g., as with a reaction sodium nitrite or pentinyl nitrite in ice water) followed by treatment of the mixture with a metal salt or other derivative of Y to obtain the variety of Y-substituted derivatives. The Y-substituents involved are those as defined in formula I and include such moieties as OH, alkyl, alkoxy, hydroxy lower alkyl, amino alkyl, azido, cyano, carboxyl, CO$_2$R$_5$, COR$_5$, SO$_3$H, Br, Cl, F or (CH$_2$)$_x$SiR$_1$R$_2$R$_3$.

More specifically, Step (B-g) involves substitution of the (B-17) compounds with the foregoing enumerated Y-substituents. Preferably, the amine of B-17 is converted to N$_2^\oplus$HSO$_4^\ominus$ or N$_2^\oplus$Cl$^\ominus$ diazonium salts and by a variety of reactions the Y-substituted compounds of (B-18) are prepared. To prepare compounds wherein Y is OH, a so-prepared diazonium salt is dissolved in water, heated at about 80° to 120° C. to produce the desired hydroxy function which may be converted to its alkoxy derivative by alkylation in the presence of a base and the appropriate alkyl halide. To produce a fluoro derivative the diazonium salt (formed with BF$_4^\ominus$N$_2^\oplus$) is heated at 140° to 160° C. to obtain the desired fluoro derivatives.

For the chloro and bromo the diazonium sulfate or chloride salt is treated with cuprous bromide or chloride to obtain the desired bromo or chloro derivatives. To obtain the azide the diazonium salt is treated with sodium azide in water. The cyano derivative is obtained by treatment of the diazonium salt with cuprous cyanide. The carboxy moiety may be obtained by hydrolysis (in a basic aqueous medium) of the cyano moiety and, if desired, the acid may be esterified with the appropriate R$_5$ alcohol, in the presence of DCC and DMAP, to obtain the appropriate —CO$_2$R$_5$ moiety. The —SO$_3$H moiety may be obtained by treating the diazonium salt with cupric chloride in the presence of HCl to obtain the SO$_2$Cl moiety which, when treated with water, gives the desired —SO$_3$H moiety. To obtain the desired —COR$_5$ moiety the diazonium salt is treated with an oxime [R$_5$CH= NOH] in the presence of copper sulfate and sodium sulfite, the resulting oxime is hydrolized to obtain the reduced desired acyl moiety (Y is [O=C—R$_5$]), the ketone of which is with sodium borohydride and the resulting alcohol phthalamide (HOCR$_5$) is subjected to a Mitsunobu reaction to form a which, upon treatment with hydrazine, is cleared a —SiR$_1$R$_2$R$_3$ to obtain the H$_2$N—C—R$_5$ amine. In those instances wherein Y is substituent the starting compound is a tribromobenzene which is treated as in Step (A-a) except that two equivalents of magnesium and ClSiR$_1$R$_2$R$_3$ are used to obtain the derivative corresponding to (B-16) which by Step (A-b) is converted to (B-20) wherein Y is a —SiR$_1$R$_2$R$_3$ moiety.

Following the formation of the Y-substituted compounds of formula (B-18), step (B-h) is employed to remove the alcohol-protecting group by hydrolysis (e.g., Ac) under basic or acidic conditions (taking in consideration of the now-present Y-substituents) according to principles and techniques well-known and understood by those of ordinary skill in the art. The resulting alcohols (B-19) are subjected to Step (B-i) wherein the alcohol is oxidized with pyridinium dichromate or with the Dess-Martin periodane oxidant in dichloromethane or with the Swern reaction to produce compounds (B-20). Alternatively, the alcohols may be esterified, as described above, with an acyl halide.

In those instances wherein it is desired to prepare compounds of formula I represented by the sub-generic formula

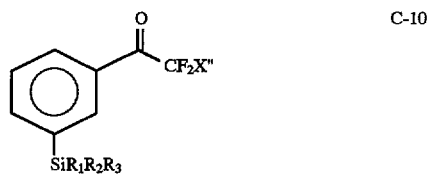

C-10 i.e., those compounds wherein n and m are zero, Y is H, and X' is $COR_9$, $CO_2R_5$, $CONHR_5$ or $COR_6$, it is preferred to utilize the process of the following reaction scheme.

Reaction Scheme C

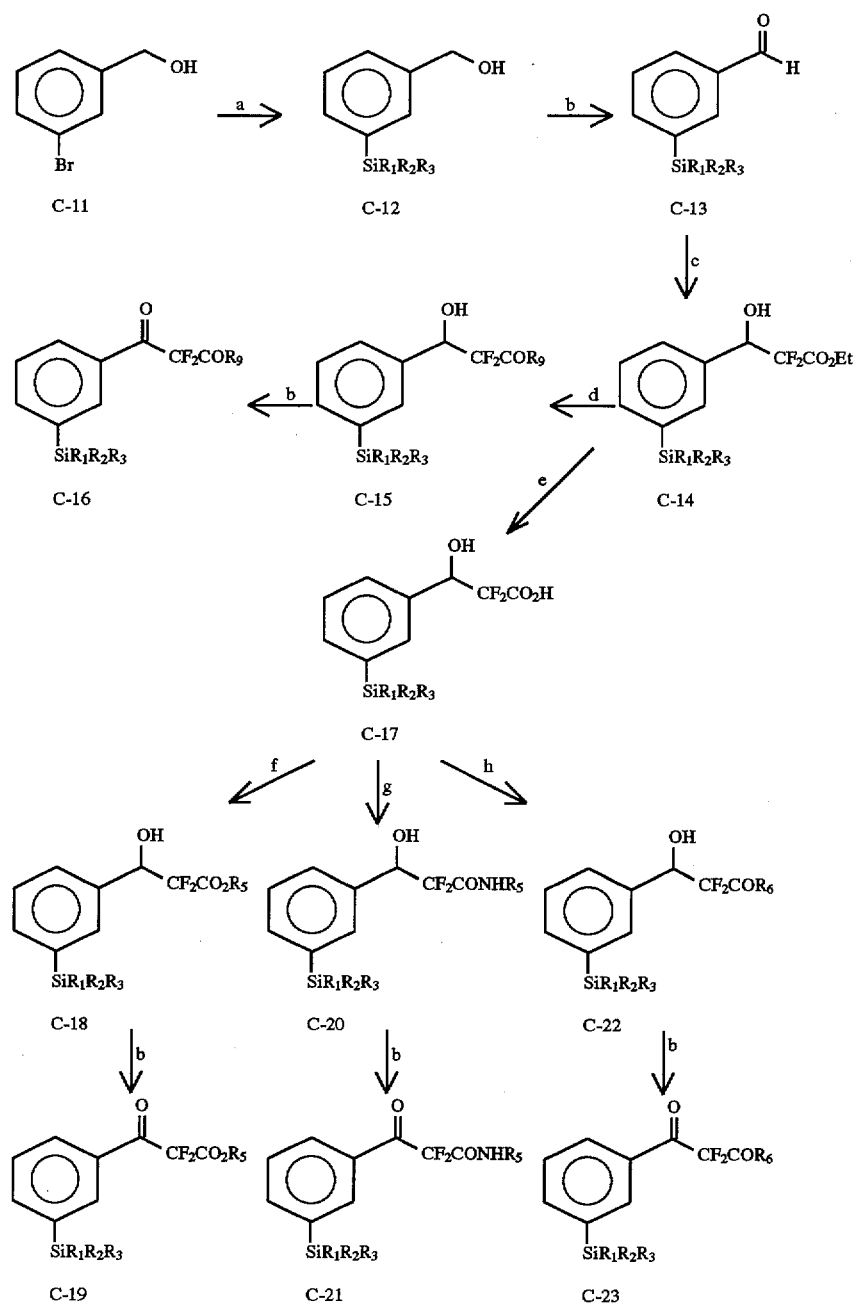

Step (C-a) involves the treatment of 3-bromobenzylalcohol (C-11) with 2 equivalents of butyl lithium in diethyl ether at 0° C., treat the resulting lithio derivatives with 2 equivalents of the desired ClSiR₁R₂R₃ and stir the resulting mixture at room temperature until the reaction is complete (generally 15–24 hours). Hydrolize, and after extraction, treat the crude product in 90% aqueous methanol for one hour at reflux temperature to obtain the silylated alcohols (C-12). Step (C-b) oxidizes the alcohols with pyridinium dichromate in dichloromethane to obtain the aldehydes (C-13) which, in Step (C-c), are treated with an alkyl bromo difluoroacetate in THF in the presence of zinc at reflux temperatures to obtain intermediary hydroxy difluoroesters (C-14). In Step (C-d) these esters (C-14) are treated with two equivalents of a metallo derivative, preferably a lithium or magnesium derivative of the $R_9$ moiety, in diethyl ether or THF to obtain compounds (C-15) which, as in Step (C-b) are oxidized to their corresponding ketones (C-16) using pyridinium dichromate or the Swern or Dess-Martin reactions. Alternatively, using Step (C-e) the hydroxy difluoro esters of formula (C-14) may be hydrolized by treatment with lithium hydroxide in 80% aqueous ethylene glycol dimethylether to obtain the corresponding hydroxy difluoro acids (C-17). These acids, using Step (C-f) may be treated with an alcohol ($R_5$OH) in the presence of dicyclohexyl carbodiimide and 4-dimethylamino pyridine to obtain the esters (C-18). Alternatively, using Step (C-g) the acids (C-17) may be treated with an amine ($R_5NH_2$) in the presence of dicyclohexylcarbodiimide and 1-hydroxybenzotriazole to obtain the amides of formula (C-20). Using Step (C-h) the hydroxy difluoro acids (C-17) may also be reacted with a natural occurring amino acid, or a peptide $R_6H$ in the dicyclohexylcarbodiimide and 1-hydroxybenzotriazole to obtain the products of formula (C-22). In each instance, using the oxidation step of (C-b), the alcohols of (C-15), (C-18), (C-20) and (C-22) may be oxidized to the corresponding ketones of formulae (C-16), (C-19), (C-21) and (C-23), respectively, or they may be esterified, as described above, with an acyl halide.

In those instances wherein it is desired to prepare compounds of the subgeneric formula

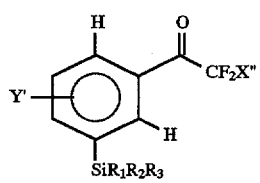
D-10 i.e., those compounds wherein n and m are zero,

Y' is other than H,

X" is $COR_9$, $CO_2R_5$, $CONHR_5$ or $COR_6$, the following reaction scheme is utilized.

Reaction Scheme D

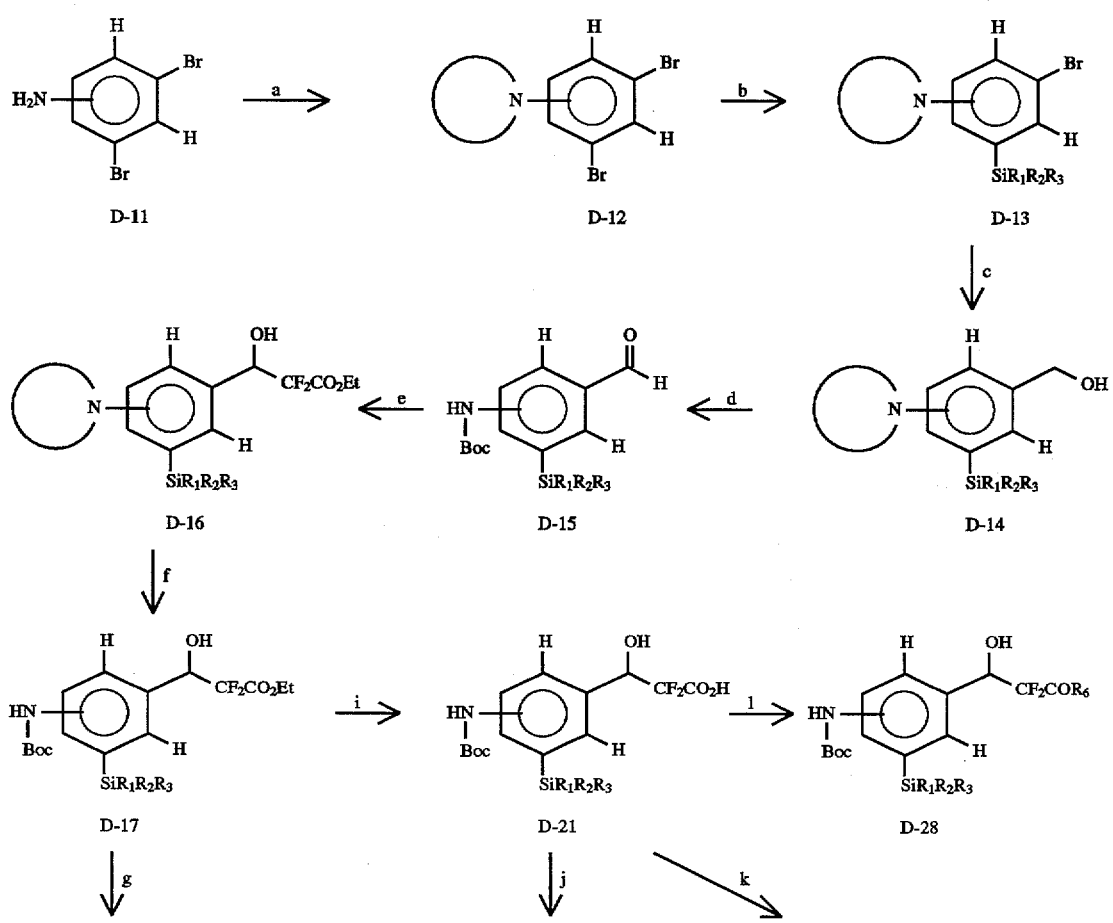

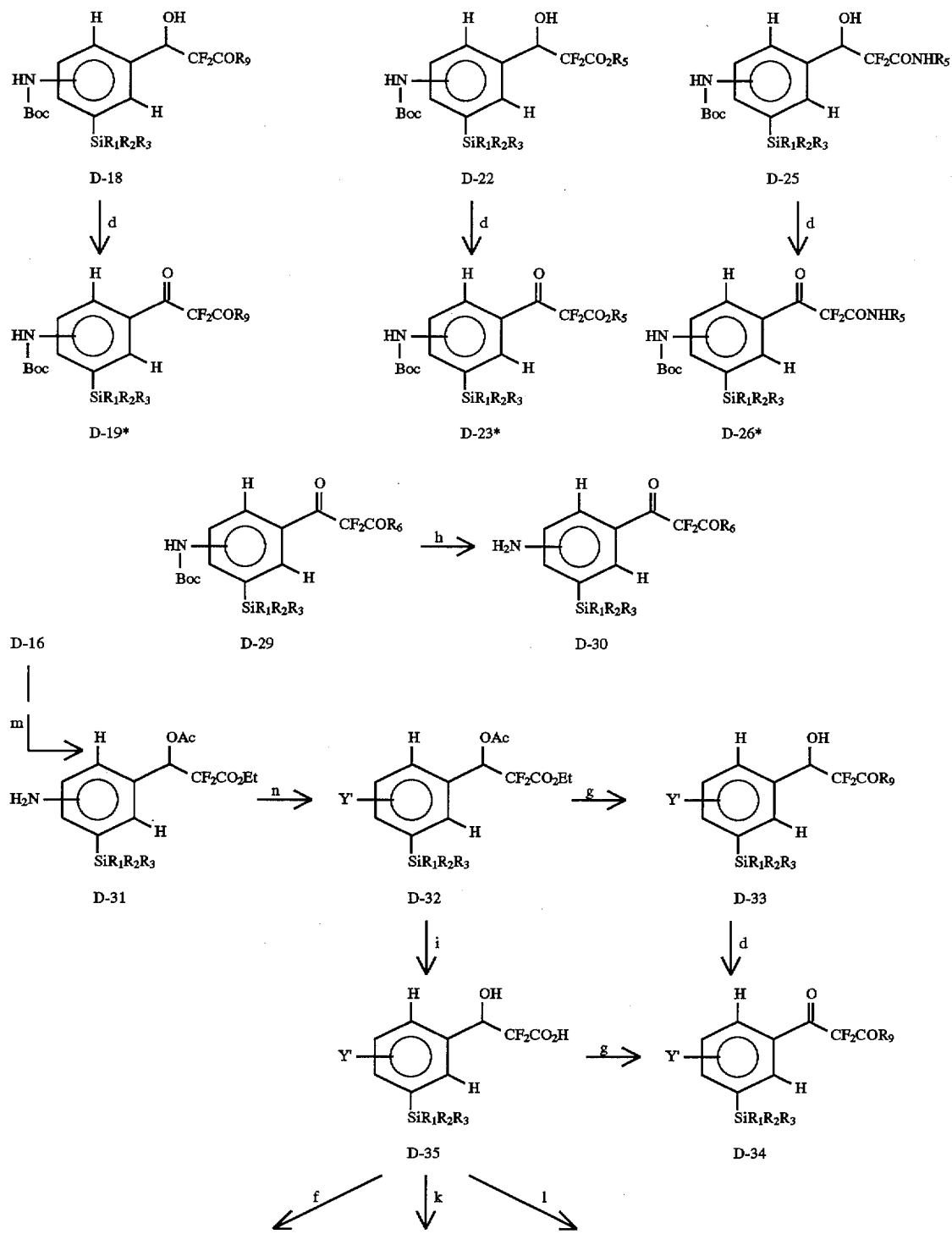

-continued
Reaction Scheme D

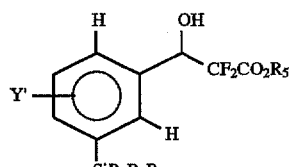
D-36

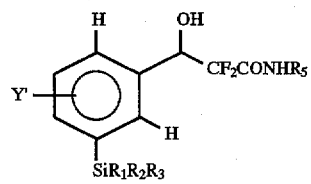
D-38

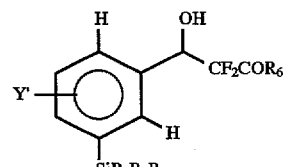
D-40

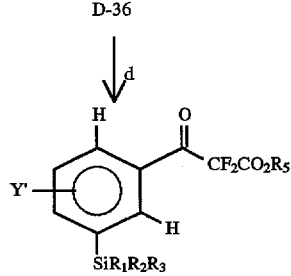
D-37

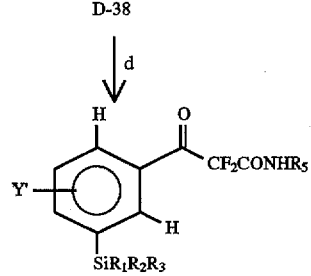
D-39

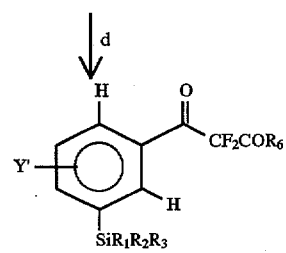
D-41

[*Compounds (D-19), (D-23), and (D-26) are de-Boced to desired compounds (D-20), (D-24), and (D-27) according to step D-h.]

Compound (D-13) is obtained according to Steps (D-a) and (D-b) using proceses (B-a) and (B-b).

The stabase adducts (D-13), using Step (D-c) are reacted with one equivalent of magnesium in diethylether and the resulting in situ intermediate treated with paraformaldehyde (followed by hydrolysis with saturated aqueous ammonium chloride solution) to form the appropriate hydroxymethyl compounds (D-14) which, using Step (D-d), are oxidized according to Step (C-b) and the resulting aldehydes (D-15) using Step (D-e) are converted to their esters (D-16) according to (C-c). Using Step (D-f) these esters are treated with 1N HCl to convert the stabase adduct to its amine and the amine is protected with a Boc protecting group to produce compounds (D-17). These intermediates [using Steps (D-g), (D-d) and (D-h)] are sequentially converted to compounds (D-18), (D-19) and (D-20) using the processes described for Step (C-d) (using 3 equivalents of the metallo derivatives of $R_5$), Step (C-b) and Step (D-h) which is treatment of the Boc derivatives with a solution of HCl in diethyl ether. Compounds (D-17) may also be sequentially converted to (D-21) by Step (D-i) [as described in Step (C-e)], then by Step (D-f) to (D-22), then by Step (D-d) [as described in (C-b)] to (D-23), then by Step (D-h) to (D-24).

Compounds (D-21) also may be sequentially treated according to Step (D-k) (see C-g) to obtain (D-25) which are converted to (D-26) according to Step (D-d) (see C-b) and to (D-27) according to Step (D-h). Compounds (D-21) also may be sequentially treated according to Step (D-l) (see C-h) to produce (D-28) to (D-29) according to Step (D-d) (see C-b) and then to compounds (D-30) by Step (D-h).

From compound (D-16), compounds (D-34), (D-37), (D-39) and (D-41) may be obtained using the above described chemistry. The alcohols of (D-33), (D-36), (D-38), and (D-40) may be oxidized to their ketones or they may be converted to their esters as hereinabove described.

To prepare compounds of formula

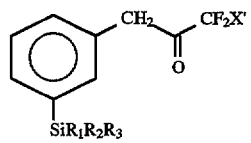
E-10 i.e., compounds wherein
n is one,
m is zero,
Y is H, and
X' is H, Br, Cl, F or $R_4$, the following reaction scheme is utilized Reaction Scheme E

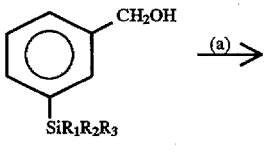
E-11

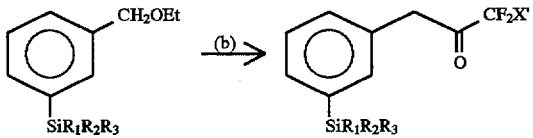
E-12    E-13

In this sequence, silylated compounds (E-11) are treated with n-butyllithium and then with ethyl iodide to produce compounds (E-12) which, by treatment with six equivalents of lithium in diethyl ether or THF at −10° C., produce an in situ intermediate to which is added an acid, ester (X'CF$_2$CO$_2$R wherein R is H or $C_{1-6}$ alkyl) or an acid chloride (X'CF$_2$COCl), followed by hydrolysis with 1N HCl to obtain compounds (E-13). These ketones may be reduced with sodium borohydride or sodium cyano borohydride by reaction in ethanol followed by hydrolysis with saturated ammonium chloride and the resulting alcohols esterified with an acyl halide (ClC(O)R with R being H or $C_{1-10}$ alkyl), in the presence of TEA (or neat pyridine) in a suitable solvent such as dichloromethane; both these reactions being effected according to well known and understood reaction conditions.

To prepare compounds of formula

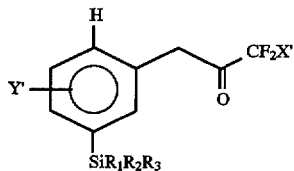

i.e., compounds wherein
n is one,
m is zero,
Y' is other than H, and
X' is H, Br, Cl, F or $R_4$, the following reaction scheme is utilized.

Step (F-a) forms the stabase adduct (F-12) with process (B-a).

Step (F-b) silylates (F-12) to (F-13) with process (A-a).

Step (F-c) treats ((F-13) with butyllithium at 0° C. in ether or THF and then treats with dibromomethane to obtain (F-14).

Step (F-d) treats (F-14) with magnesium in diethyl ether or THF at reflux, then at −78° C. intermediate is treated with ester (X'CF$_2$CO$_2$R) or acid chloride (X'CF$_2$COCl), followed by hydrolysis with 1N HCl to obtain (F-15).

Step (F-e) treats (F-14) as in Step (F-d) except the hydrolysis is effected with an ammonium chloride solution to obtain (F-16).

Step (F-f) treats (F-16) according to process (B-e) to obtain (F-17).

Step (F-g) treats (F-17) according to process (B-f) to obtain (F-18).

Step (F-h) treats (F-18) according to process (B-g) to obtain (F-19).

Reaction Scheme F

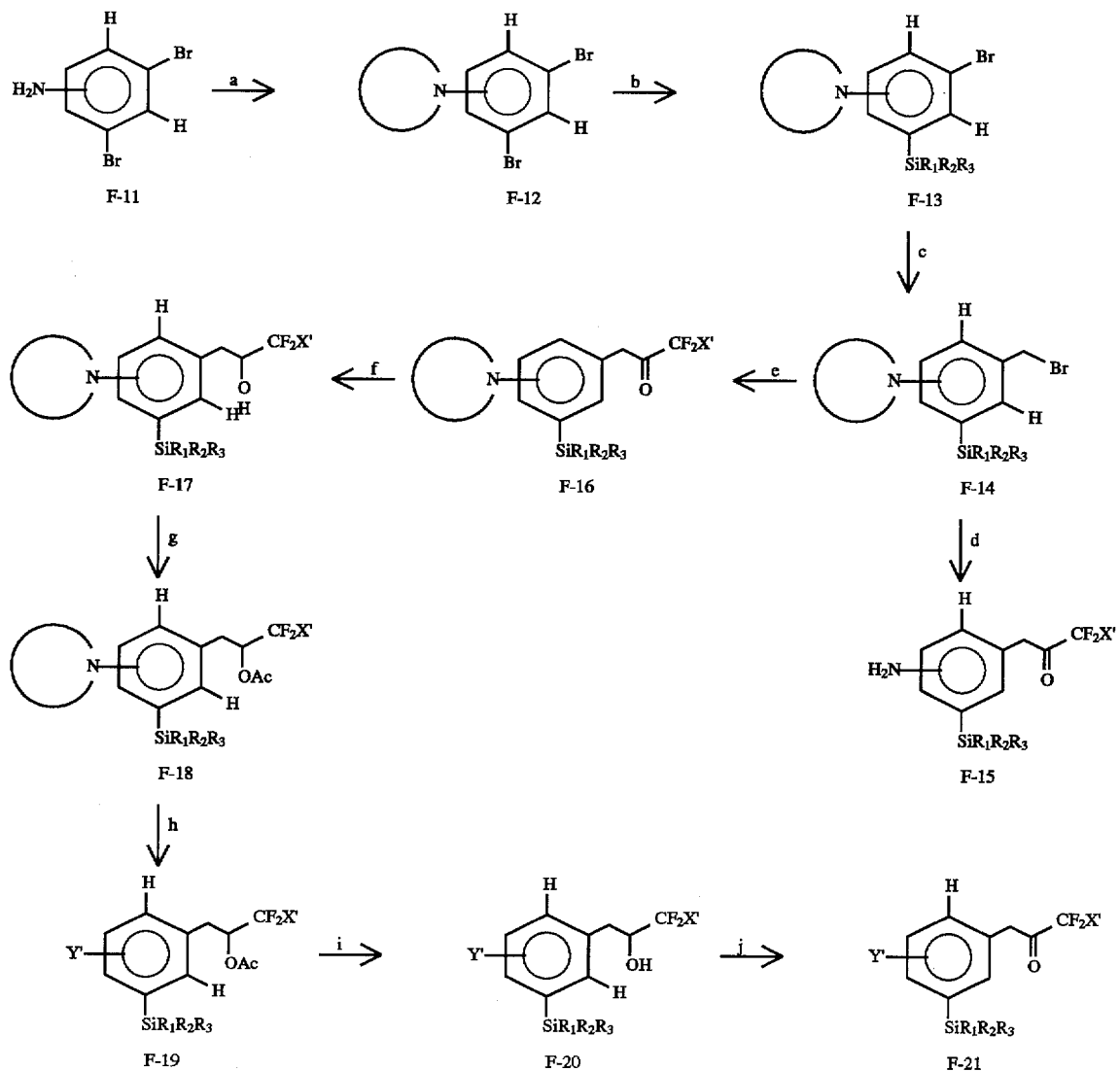

Step (F-i) treats (F-19) according to process (B-h) to obtain (F-20).

Step (F-j) treats (F-20) according to process (B-i) to obtain (F-21). The alcohols (F-20) may also be esterified with an acyl halide as hereinabove described.

i.e., compounds wherein
n is one,
m is zero,
Y is H, and
X" is $COR_9$, $CO_2R_5$, $CONHR_5$ or $COR_6$, the following reaction scheme is utilized.

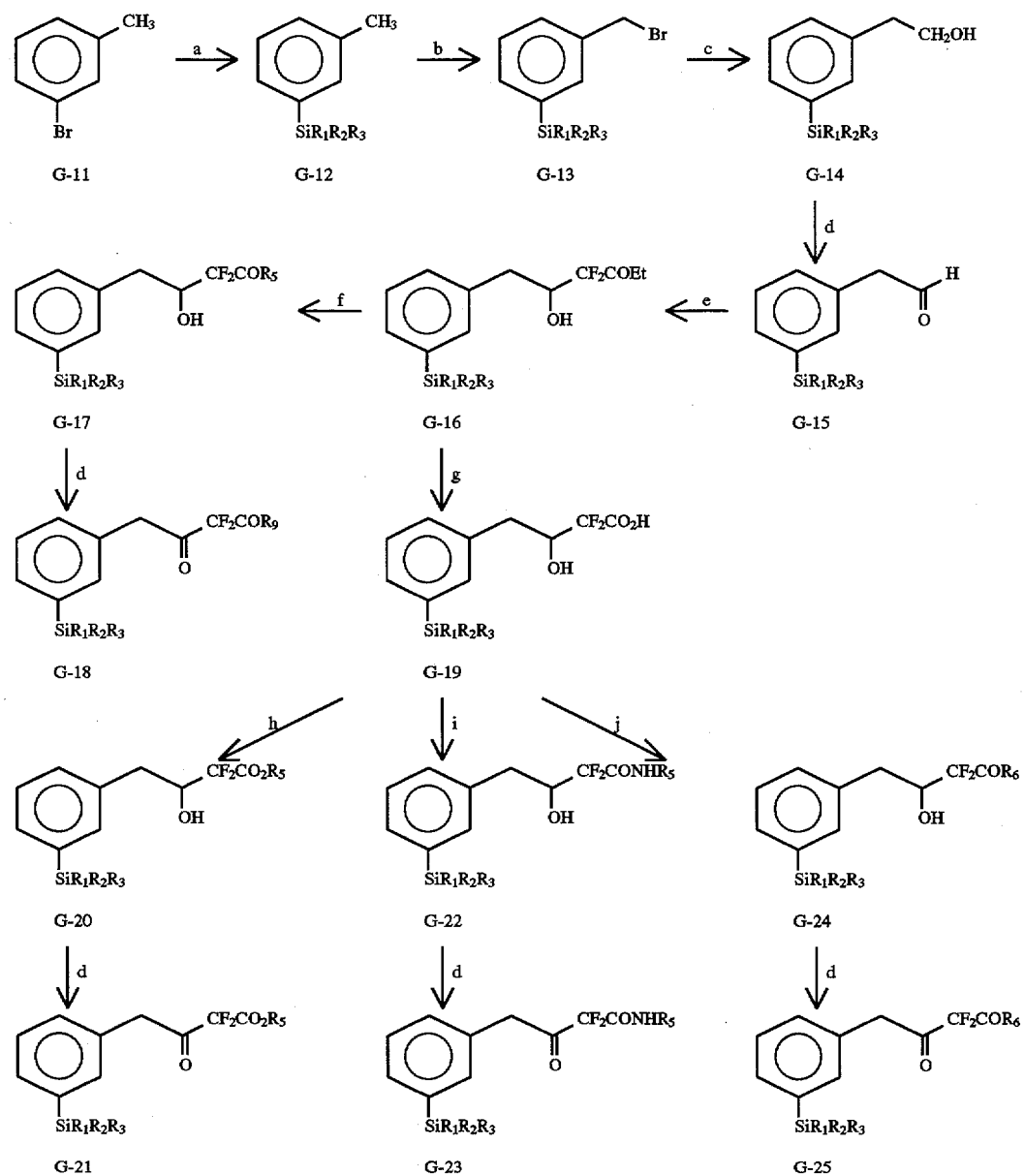

To prepare compounds of formula

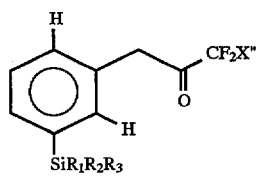

G-10

Step (G-a) silylates compounds (G-11) to form compounds (G-12) according to process (A-a).
Step (G-b) treats compounds (G-12) to form compounds (G-13) by treatment with one equivalent of N-bromosuccinamide in $CCl_4$ at reflux temperatures.
Step (G-c) treats compounds (G-13) according to process (D-c) to obtain compounds (G-14).
Step (G-d) treats compounds (G-14), (G-17), (G-20), (G-22) and (G-24) according to process (C-b) to obtain compounds (G-15), (G-18), (G-21), (G-23) and (G-25).

Step (G-e) treats compounds (G-15) according to process (C-c) to obtain compounds (G-16).
Step (G-f) treats compounds (G-16) according to process (C-d) to obtain compounds (G-17).
Step (G-g) treats compounds (G-16) according to process (C-e) to obtain compounds (G-19).
Step (G-h) treats compounds (G-19) according to process (C-f) to obtain compounds (G-20).
Step (G-i) treats compounds (G-19) according to process (C-g) to obtain products (G-22).
Step (G-j) treats compounds (G-19) according to process (C-h) to obtain compounds (G-24). The alcohols of (G-17), (G-21), (G-23), and (G-25) may also be esterified with an acyl halide as hereinabove described.

To prepare compounds of formula

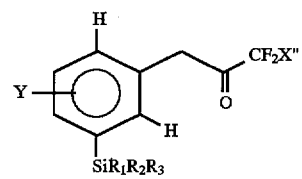

i.e., compounds wherein
n is one,
m is zero,
Y is other than H, and
X" is $COR_9$, $CO_2R_5$, $CONHR_5$ or $COR_6$, the following reaction scheme is utilized.

Reaction Scheme H

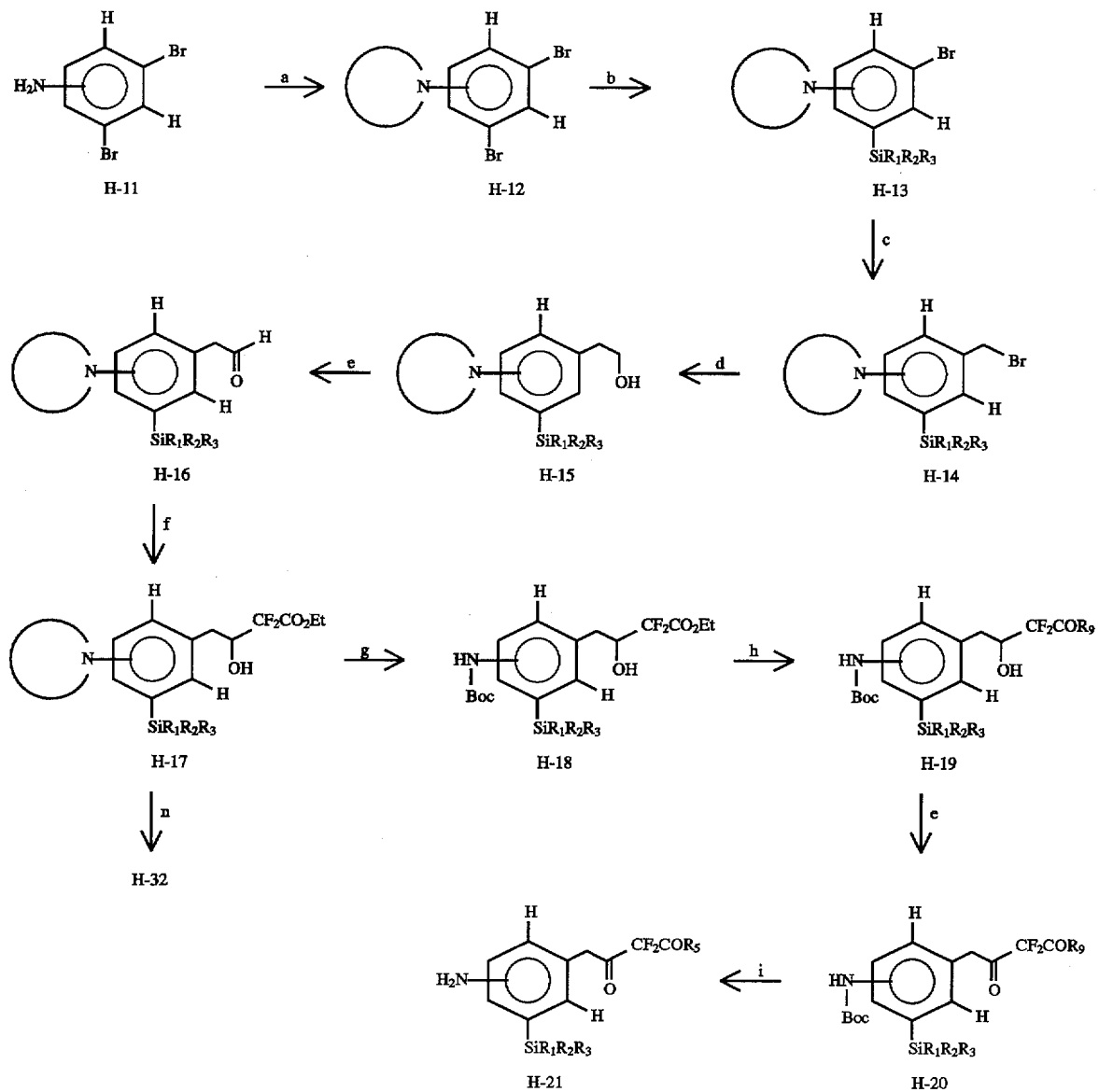

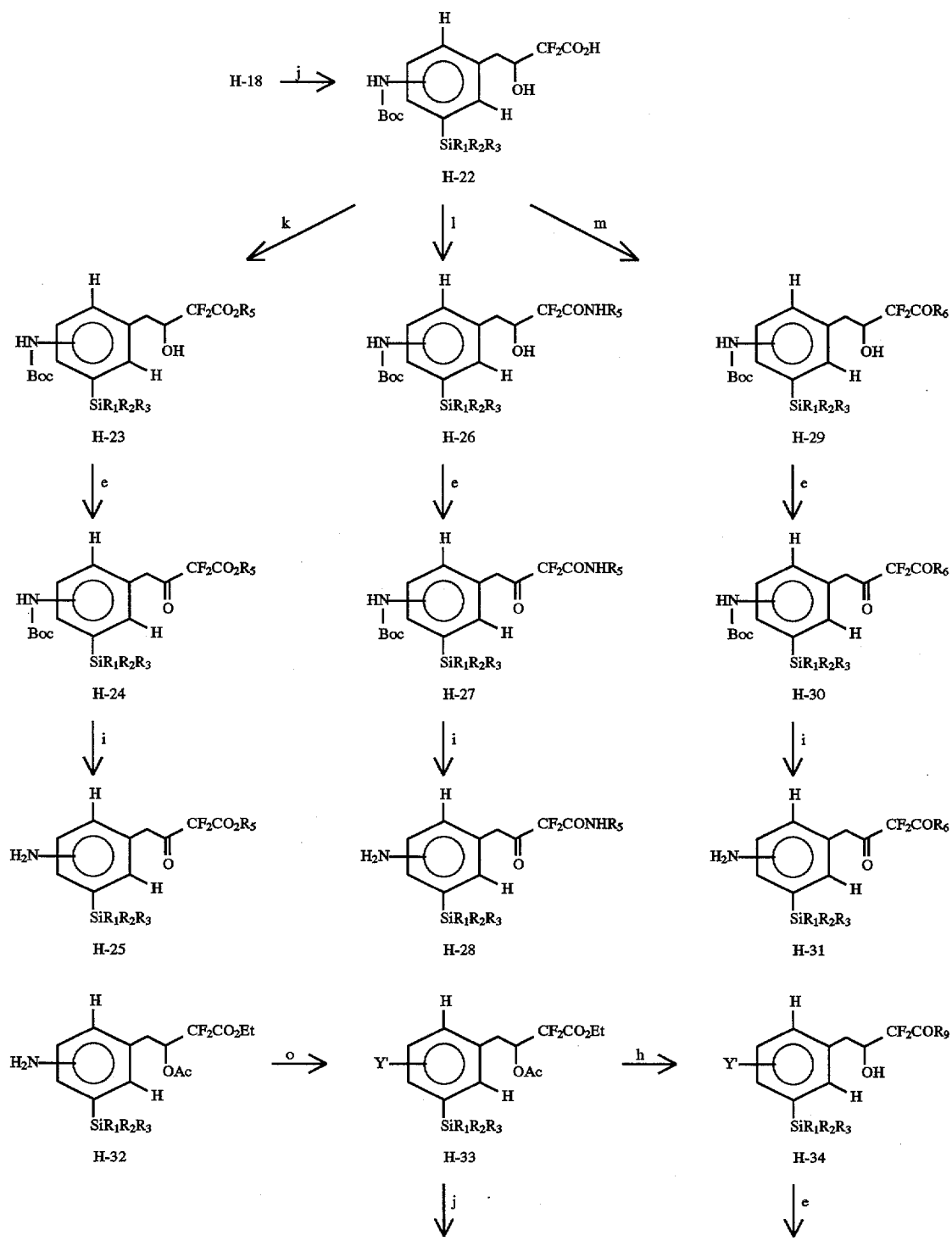

-continued
Reaction Scheme H

Step (H-a) converts compounds (H-11) to their stabase adducts according to the process of (B-a) to obtain compounds (H-12).

Step (H-b) converts compounds (H-12) to compounds (H-13) according to process (B-a).

Step (H-c) converts compounds (H-13) according to process (F-c) to obtain products (H-14).

Step (H-d) converts compounds (H-14) according to process (D-c) to obtain products (H-15).

Step (H-e) converts compounds (H-15), (H-19), (H-23), (H-26) and (H-29) according to process (C-b) to obtain products (H-16), (H-20), (H-24), (H-27) and (H-30), respectively.

Step (H-f) converts compounds (H-16) according to process (C-c) to obtain products (H-17).

Step (H-g) converts compounds (H-17) according to process (D-f) to obtain products (H-18).

Step (H-h) converts compounds (H-18) according to process (C-f) to obtain products (H-19).

Step (H-i) converts compounds (H-20), (H-24), (H-27) and (H-30) according to process (D-h) to obtain products (H-21), (H-25), (H-28) and (H-31), respectively.

Step (H-j) converts compounds (H-18) according to process (C-e) to obtain products (H-22).

Step (H-k) converts compounds (H-22) according to process (C-f) to obtain products (H-23).

Step (H-l) converts compounds (H-22) according to process (C-g) to obtain products (H-26).

Step (H-m) converts compounds (H-22) according to process (C-h) to obtain products (H-29).

Step (H-n) converts compounds (H-17) according to process (B-f) to obtain products (H-32).

Step (H-o) converts compounds (H-32) according to process (B-g) to obtain products (H-33).

Compound (H-33) is converted to compounds (H-35), (H-38), (H-40), (H-42) according to the appropriate above-described processes. The alcohols of (H-34), (H-37), (H-38), and (H-41) may also be esterified with an acyl halide as hereinabove describe.

To prepare compounds of formula i.e., compounds wherein n is zero, m is one,

Y is H, and

X' is H, Br, Cl, F or $R_4$, the following reaction scheme is utilized

Reaction Scheme I

-continued
Reaction Scheme I

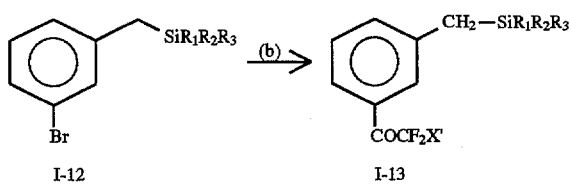

Step (I-a) converts compounds (I-11) according to process (A-a) to obtain products (I-12).

Step (I-b) converts compounds (I-12) according to process (A-b) to obtain products (I-13). The ketones may be reduced with sodium borohydride or sodium cyano borohydride by reaction in ethanol followed by hydrolysis with saturated ammonium chloride and the resulting alcohols esterified with an acyl halide (ClC(O)R with R being H or $C_{1-10}$ alkyl), in the presence of TEA (or neat pyridine) in a suitable solvent such as dichloromethane; both these reactions being effected according to well known and understood reaction conditions.

To prepare compounds of formula

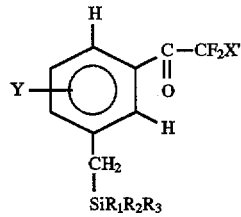

i.e., compounds wherein n is zero, m is one,

Y' is other than H, and

X' is H, Br, Cl, F or $R_4$, the following reaction scheme is utilized.

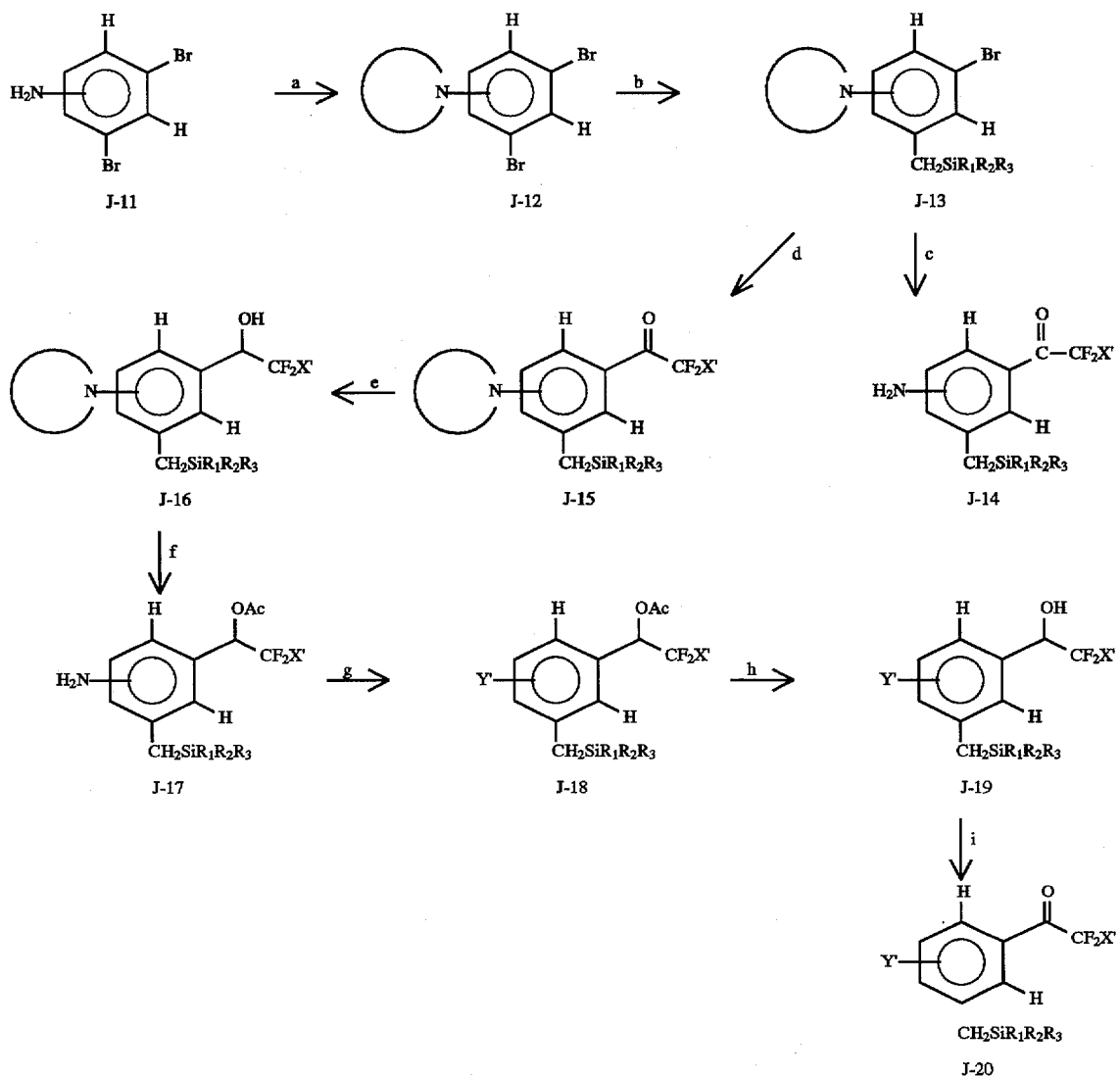

Step (J-a) converts compounds (J-11) to their stabase adduct as described in (B-a).

Step (J-b) converts compounds (J-12) to their silylated derivatives (J-13) using one equivalent of $ICH_2SiR_1R_2R_3$ after treatment of (J-12) with butyl lithium in ether at 0° C. as in above-described silylating procedures.

Step (J-c) converts compounds (J-13) to (J-14) using procedures analogous to Step (B-c).

Step (J-d) converts compounds (J-13) to (J-15) using procedures analogous to Step (B-d).

Step (J-e) converts compounds (J-15) to (J-16) using procedures analogous to Step (B-e).

Step (J-f) converts compounds (J-16) to (J-17) using procedures analogous to Step (B-f).

Step (J-g) converts compounds (J-17) to (J-18) using procedures analogous to Step (B-g).

To prepare compounds of formula

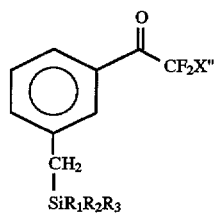

K-10 wherein
m is one,
n is zero,
Y is H, and
X" is $COR_9$, $CO_2R_5$, $CONHR_5$ or $COR_6$, the following reaction scheme is utilized.

Reaction Scheme K

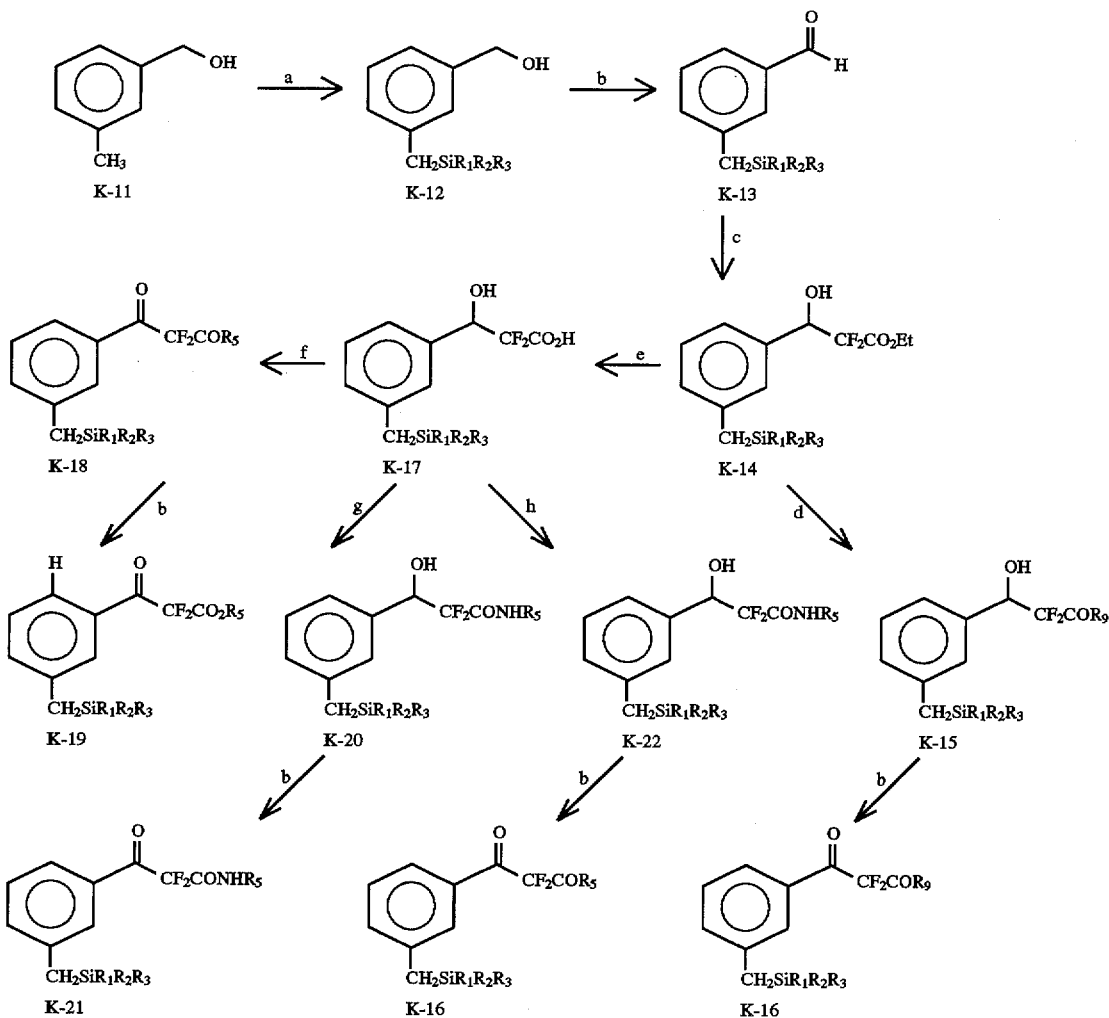

Step (J-h) converts compounds (J-18) to (J-19) using procedures analogous to Step (B-h).

Step (J-i) converts compounds (J-19) to (J-20) using procedures analogous to Step (B-i). The alcohols (J-19) may also be esterified, as described above, with an acyl halide.

Step (K-a) converts 3-methylbenzyl alcohol (K-11) to (K-12) by treatment with 3 equivalents of butyllithium at −20° C. in diglyme, followed by treatment with 3 equivalents of $ClSiR_1R_2R_3$ and triethylamine at room temperature, followed by refluxing the extracted crude product in 90% aqueous methanol to obtain the desired silylated product.

Step (K-b) converts (K-12) to compounds (K-13) using procedures analogous to (C-b).

Step (K-c) converts (K-13) to compounds (K-14) using procedures analogous to (C-c).

Step (K-e) converts (K-14) to compounds (K-17) using procedures analogous to (C-e).

Steps (K-f) and (K-b) using procedures analogous to (C-f) and (C-b) produce (K-19).

Steps (K-g) and (K-b) using procedures analogous to (C-g) and (C-b) produce (K-21).

Steps (K-h) and (K-b) using procedures analogous to (C-g) and (C-b) produce (K-23).

Steps (K-d) and (K-b) using procedures analogous to (C-d) and (C-b) produce (K-16). The alcohols of (K-14), (K-15), (K-18), (K-20), and (K-22) may also be esterified, as described above, with an acyl halide.

To prepare compounds of formula I represented by the subgeneric formula

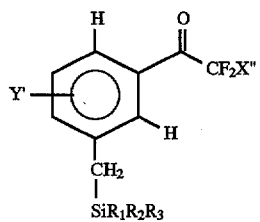
L-10 i.e., compounds wherein m is one, n is zero,

Y' is other than H, and

X" is $COR_9$, $CO_2R_5$, $CONHR_5$ or $COR_6$, the following reaction scheme is utilized.

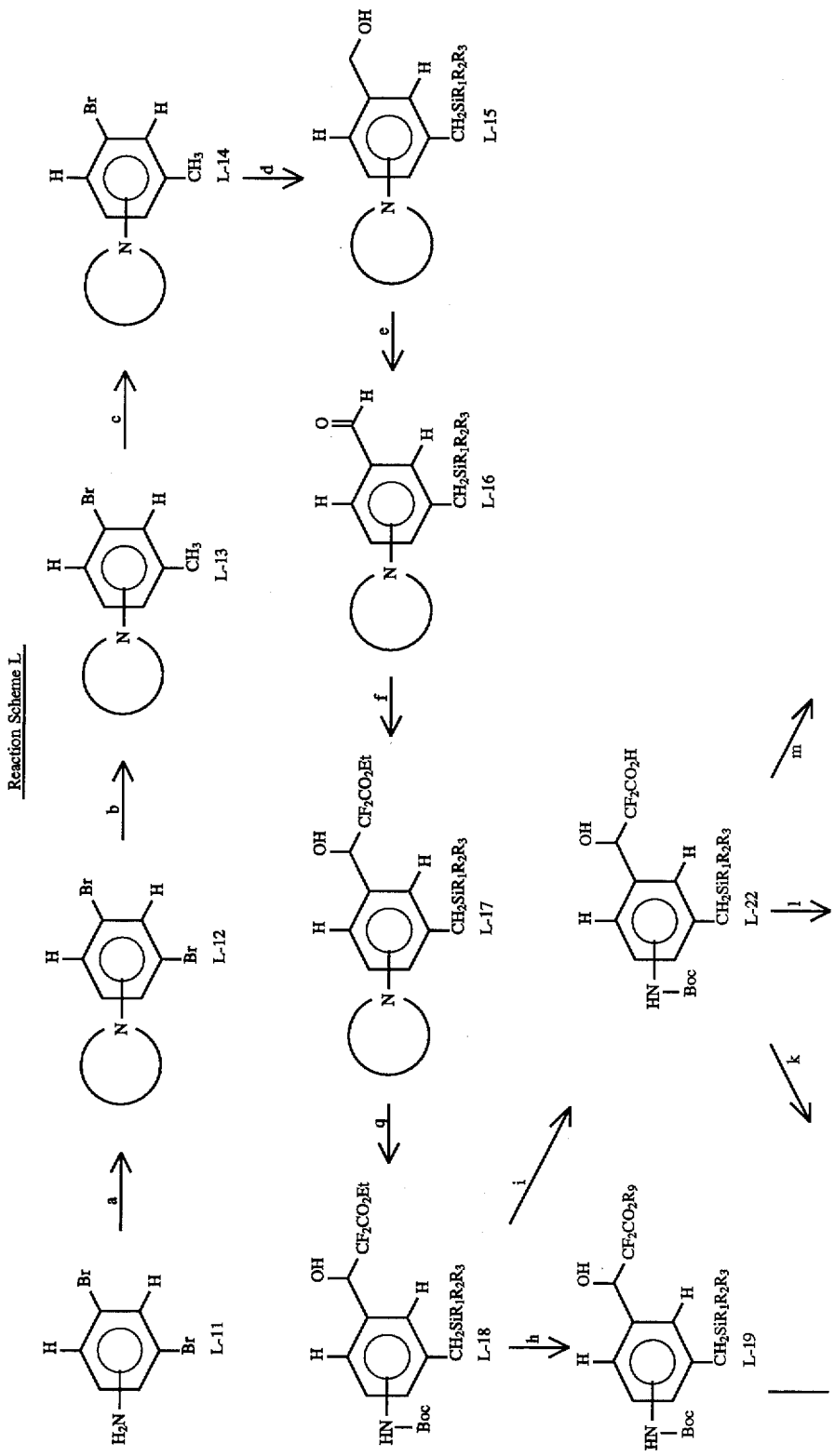
Reaction Scheme L

-continued
Reaction Scheme L
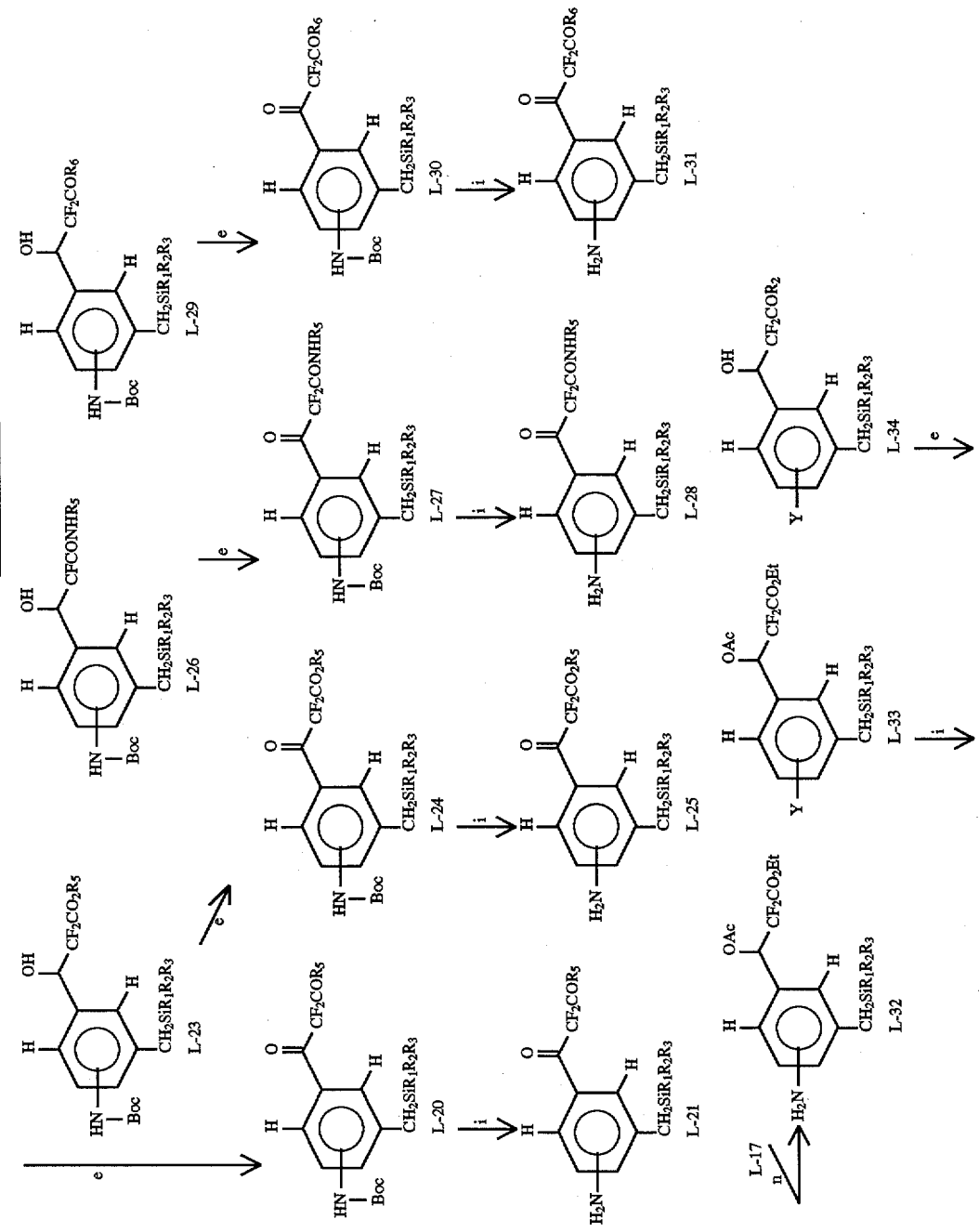

-continued
Reaction Scheme L
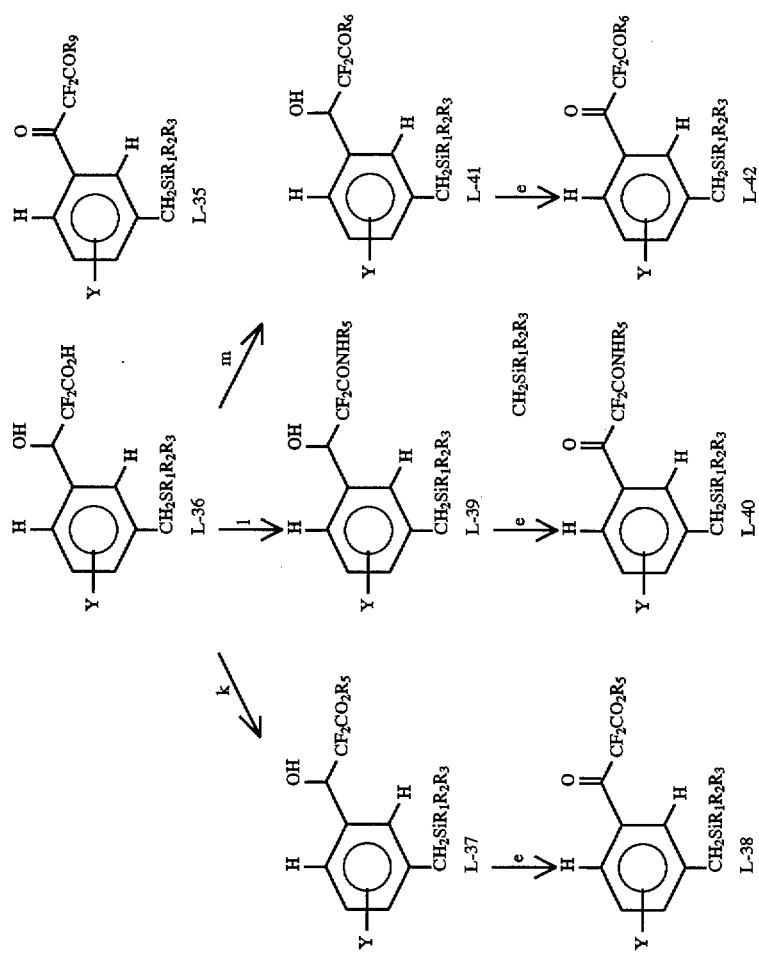

The compounds of subgeneric formula

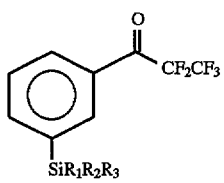

i.e., those compounds of formula 1 wherein Z is —C(O)CF$_2$CF$_3$, m and n are zero, and Y is H, may be prepared by the following reaction scheme:

Reaction Scheme M

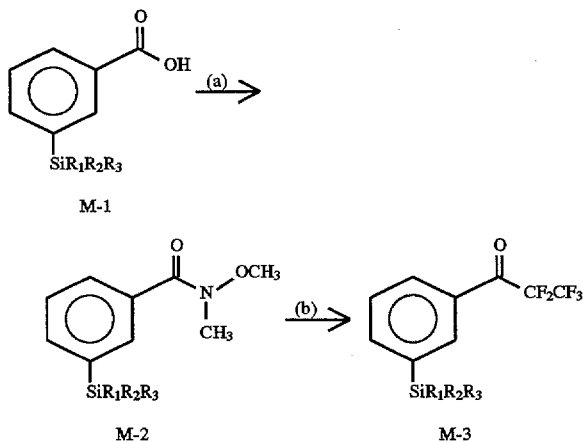

wherein R$_1$, R$_2$, and R$_3$ are as defined in formula I. In the initial step (M-a) the reaction involves the treatment of silylbenzoic acid with isobutylchloroformate and subsequently N,O-dimethylhydroxylamine. This reaction can be performed by adding 1.1 equivalents of isobutylchloroformate to a solution of 1.0 equivalents of silylbenzoic acid in methylene chloride, preferably cooled to about –22° C. to which N-methylmorpholine has been added previously. A solvent such as methylene chloride can be advantageously employed. After stirring for from about 5 minutes to about 1 hour, preferably about 25 minutes, 3 equivalents of N,O-dimethylhydroxylamine hydrochloride is added. The reaction is allowed to proceed for from about 1 hour to about 10 hours, at from about –40° C. to about 50° C. A preferred procedure calls for the reaction to proceed for 1 hour at –22° C. and then an additional 1½ hours at room temperature. The reaction is quenched with dilute acid such as dilute hydrochloric acid and the product is then isolated from the aqueous phase by, for example, by extracting with an immisible solvent such as diethyl ether, washing the combined extracts with a weak base, such as sodium bicarbonate, and solvent removal. Preliminary purification can be achieved by, for example, chromatography on silica gel eluting with 10% ethyl acetate in hexane.

The initial product, M-2, is then treated with a pentafluoroethyl anion generated in situ by contacting pentafluoroethyl iodide with methyllithiumlithiumbromide complex in an inert solvent such as an ethereal solvent, for example, tetrahydrofuran or diethyl ether. The reaction is performed at a cool temperature such as from about –100° C. to about –25° C., conveniently at about –78° C. and is allowed to proceed for from about 1 minute to about 1 hour. The reaction is quenched by allowing the mixture to warm to about 0° C. to about room temperature and subsequent addition of dilute acid such as dilute hydrochloric acid. The product is isolated from the aqueous phase by extraction into a water immisible solvent such as diethyl ether, washing with a weak base such as sodium bicarbonate, drying and solvent removal. Purification can be accomplished by chromatography on, for example, silica gel eluting with 10% ethyl acetate in hexane.

The compounds of subgeneric formula

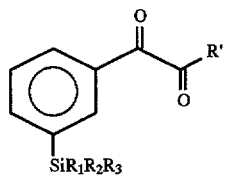

wherein R', R$_1$, R$_2$, and R$_3$ are as defined in formula I, are prepared as shown in the following scheme:

Reaction Scheme N

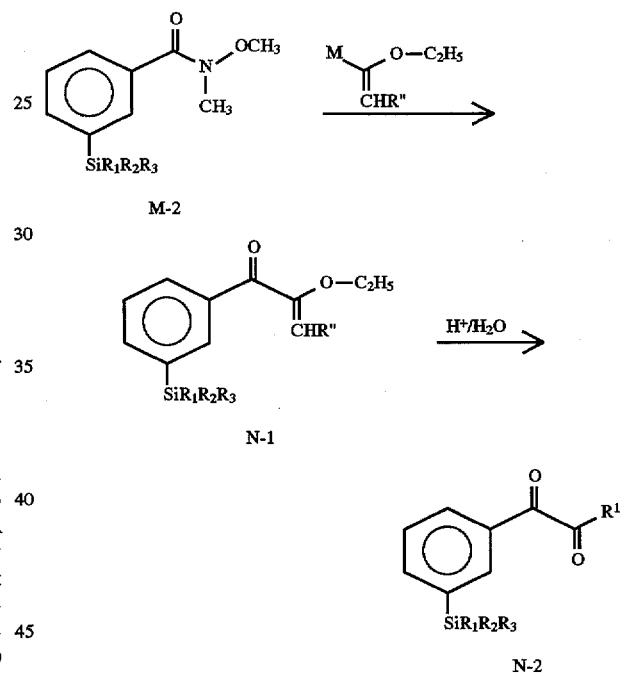

wherein R$_1$, R$_2$ and R$_3$ are as defined in formula I and R" is selected such that it produces the desired R' group. The preparation of the M-2 compounds is described above. The M-2 compound is then reacted with an appropriate Grignard or lithium ethyl vinyl ether using standard reaction conditions such as contacting the reactants together in an inert solvent, preferably tetrahydrofuran, at temperatures of about –20° C. to 0° C. The Grignard, if used, is freshly prepared from an organo lithium species, e.g., t-butyl lithium added to ethyl vinyl ether which is converted to an ethyl vinyl ether Grignard reagent by reaction with magnesium bromide using standard procedures well known in the art. The M-2 compounds are added to the Grignard or lithium reagent to form an in situ complex which is converted to an α-keto vinyl ether N-1 said α-keto vinyl ether being converted by treatment with hydrochloric acid in a dioxane-water mixture or any other inert solvent such as tetrahydroguran, to the desired diketones of N-2.

The compounds of formula I which are analogs of the M-3 and N-2 compounds but wherein Y is other than H and m is 1, can be prepared in a manner analagous to the preparation of the other such compounds described above.

EXAMPLE 1

2,2,2-Trifluoro-1-(3-trimethylsilylphenyl) ethanone
Step A:
3-Trimethylsilyl-bromobenzene A mixture of 1,3-dibromobenzene (25.0 g, 106.4 mmol) and trimethylsilylchloride (11.6 g, 106.4 mmol) in diethyl ether (50 ml) was added dropwise in 1½ hours on magnesium (2.59 g, 106.4 mmol) in diethyl ether (25 ml). Then the mixture was refluxed for 18 hours, cooled to 0° C., treated with 4N HCl (75 ml). The organic layer was separated, washed with water, brine, dried over $MgSO_4$ and concentrated. 3-Trimethylsilylbromobenzene was obtained by fractional distillation as a colorless oil (13.4 g, 55% yield, b.p.: 55°–62° C. (0.8 mmHg).
Step B:
2,2,2-Trifluoro-1-(3-trimethylsilylphenyl) ethanone To a solution of 3-trimethylsilyl-bromobenzene (7.62 g, 33.3 mmol) in diethyl ether (35 ml) was added at 0° C. 1.5M n-butyllithium in hexane (22.2 ml, 33.3 mmol) over 10 min. Then the mixture was allowed to react 15 min at room temperature, cooled to −78° C. and ethyltrifluoroacetate (14.2 g, 100 mmol) was added over 5 min. Then the mixture was allowed to react 15 min at −78° C., the cooling bath was removed and when the temperature rose to 0° C. 3N HCl (35 ml) was added dropwise. The organic layer was separated, washed with water, brine, dried over $MgSO_4$ and concentrated. Chromatography (silica gel, cyclohexane/diethyl ether: 90/10) followed by distillation under reduced pressure afforded the expected compound as a colorless oil (4.32 g, 53% yield), b.p. 120° C., Rf: 0.28 (cyclohexane/diethyl ether: 95/5).

EXAMPLE 2

1-[(4-Methoxy-3-trimethylsilyl)phenyl]-2,2,2-trifluoroethanone
Step A:
4-Bromo-3-trimethylsilylanisole To a solution of 2,4-dibromoanisole (13.3 g, 50 mmol) in diethyl ether (50 ml) at 0° C. was added over 20 min 1.5M butyllithium (33.4 ml) and the reaction was allowed to react 15 min at 0° C. Then trimethylsilylchloride (5.43 g, 50 mmol) in diethyl ether (20 ml) was added over 10 min and the resulting mixture was stirred 18 hours at room temperature. At 0° C. 3N HCl (50 ml) was added and the organic layer was separated, washed with water, brine, dried over $MgSO_4$ and concentrated. 4-Bromo-3-trimethylsilylanisole was purified by chromatography on silica gel (eluted with cyclohexane) as a colorless oil.
Step B:
1-[(4-Methoxy-3-trimethylsilyl)phenyl]-2,2,2-trifluoroethanone The title compound was prepared as described in Step B of Example 1. Chromatography on silica gel (cyclohexane/diethyl ether: 95/5) afforded a colorless oil (59% yield).

EXAMPLE 3

1-[(4-Hydroxy-3-trimethylsilyl)phenyl]-2,2,2-trifluoroethanone
Step A:
4-Bromo-3-trimethylsilylphenol To a solution of 2,4-dibromophenol (8.0 g, 31.75 mmol) in diethyl ether (35 ml) at 0° C. was added over 50 min 1.5M butyllithium (42.3 ml) and the mixture was stirred 2½ hours at room temperature. At 0° C. 3N HCl (100 ml) was added, the organic layer was separated, washed with water, brine, dried over $MgSO_4$ and concentrated. The crude product was dissolved in 90% aqueous methanol (50 ml) and refluxed 2 hours, then the solvents were removed and the title compound was purified by chromatography on silica gel (10% ethyl acetate in cyclohexane).
Step B:
1-[(4-Hydroxy-3-trimethylsilyl)phenyl]-2,2,2-trifluoroethanone To a solution of 4-bromo-3-trimethylsilylphenol (2.54 g, 10 mmol) in diethyl ether (10 ml) at 0° C. was added 1.5M butyllithium (13.4 ml) over 10 min and the mixture was stirred at 0° C. 15 min. At −78° C. was added ethyl trifluoroacetate (5.68 g, 40 mmol) in diethyl ether (10 ml), then the mixture was allowed to warm up to room temperature and was stirred 1 hour. At 0° C. 3N HCl (20 ml) was added, the organic layer separated, washed with water and concentrated. The crude product was dissolved in tetrahydrofuran (20 ml) and stirred 1 hour with aqueous sodium hydrogen carbonate (10 ml). The mixture was extracted with diethyl ether and the extract washed with water, brine, dried over $MgSO_4$ and concentrated. The title compound was purified by chromatography on silica gel (20% ethyl acetate in cyclohexane), followed by recrystallization in $CCl_4$. m.p. 178° C., Rf: 0.50 (cyclohexane/diethyl ether: 50/50).

EXAMPLE 4

1-(3,5-Bis-trimethylsilylphenyl)-2,2,2-trifluoroethanone
Step A:
3,5-Bis-trimethylsilyl-bromobenzene A mixture of 1,3,5-tribromobenzene (10.0 g, 31.75 mmol) and trimethylsilylchloride (6.90 g, 63.50 mmol) in diethyl ether (35 ml) was added dropwise in 1 hour on magnesium (1.55 g, 63.50 mmol) in diethyl ether (20 ml). Then the mixture was refluxed 18 hours, cooled to 0° C., treated with 4N HCl (50 ml). The organic layer was separated, washed with water, brine, dried over $MgSO_4$ and concentrated. 3,5-Bis-trimethylsilyl-bromobenzene was purified by chromatography on silica gel (eluted with heptane) as a colorless oil (5.39 g, 56% yield).
Step B:
1-(3,5-Bis-trimethylsilylphenyl)-2,2,2-trifluoroethanone The title compound was prepared as described in Step B of Example 1 in 35% yield. b.p. 170° C. (26 mmHg).

EXAMPLE 5

Ethyl-2,2-difluoro-3-keto-3-(3-trimethylsilyl)phenylpropionate
Step A:
3-Trimethylsilylbenzylalcohol To a solution of 3-bromobenzylalcohol (9.35 g, 50 mmol) in diethyl ether (50 ml) at 0° C. was added dropwise 1.5M butyllithium (66.7 ml) and the mixture was stirred 30 min. Then trimethylsilylchloride (11.39 g, 105 mmol) in diethyl ether (50 ml) was added dropwise and the mixture was stirred at room temperature 18 hours. The reaction mixture was treated with ice water (100 ml) and the organic layer extracted, washed with water, brine, dried over $MgSO_4$ and concentrated. The crude product was dissolved in 90% aqueous methanol (100 ml) and refluxed 1 hour. The solvents were removed and 3-trimethylsilylbenzylalcohol was purified by distillation.
Step B:
3-Trimethylsilylbenzaldehyde To a mixture of 3-trimethylsilylbenzylalcohol (3.60 g, 20 mmol) and pyridium dichromate (11.29 g, 30 mmol) in dichloromethane (60 ml) at 0° C. was added 3 Å molecular sieve powder (16 g) and anhydrous acetic acid (2 ml). Then the reaction was allowed to react 30 min at room temperature, stirred 20 min with celite (10 g), filtered and evaporated under reduced pressure. The residue was treated with diethyl ether (50 ml), filtered through $MgSO_4$ and concentrated. 3-trimethylsilylbenzaldehyde was purified by distillation.

Step C:
Ethyl-2,2-difluoro-3-hydroxy-3-(3-trimethylsilyl) phenylpropionate

A solution of 3-trimethylsilylbenzaldehyde (1.78 g, 10 mmol) and ethyl bromodifluoroacetate (2.23 g, 11 mmol) in tetrahydrofuran (10 ml) was added dropwise on zinc wool (7.85 g, 12 mmol) in refluxing tetrahydrofuran (10 ml). Then the reaction was allowed to react 1 hour, cooled, hydrolysed with a saturated ammonium chloride solution (20 ml) and diluted with diethyl ether (20 ml). The organic layer was washed with brine, dried over $MgSO_4$ and concentrated. The title compound was purified on silica gel (20% ethyl acetate in cyclohexane).

Step D:
Ethyl-2,2-difluoro-3-keto-3-(3-trimethylsilyl) phenylpropionate

The title compound was prepared as described in Step B and purified by distillation.

EXAMPLE 6

2,2-Difluoro-3-keto-3-(5-nitrile-3-trimethylsilyl)phenyl propanoic acid

Step A:
3,5-Dibromo-N,N-(1,1,4,4-tetramethyl-1,4-disilethylene) aniline

To a solution of 3,5-dibromoaniline (25,10 g, 100 mmol) in tetrahydrofuran (100 ml) at −30° C. was added 1.5M butyllithium (66.67 ml). Then at −78° C. was added a solution of 1,1,4,4-tetramethyl-1,4-dichlorosilethylene (21.50 g, 100 mmol) in tetrahydrofuran (100 ml) and the mixture was allowed to warm at room temperature and stirred 1 hour. The mixture was poured into water (200 ml), diluted with diethyl ether (100 ml) and the ether layer separated. The aqueous layer was washed twice with diethyl ether and the etheral extracts combined, dried over $MgSO_4$ and the solvents removed under reduced pressure. The title compound was recrystallized from hexane.

Step B:
3-Bromo-5-trimethylsilyl-N,N-(1,1,4,4-tetramethyl-1,4-disilethylene)aniline The title compound was prepared as described in Step A of Example 1, except for hydrolysis which was made with a saturated ammonium chloride solution. Purification was achieved by recrystallization from hexane.

Step C:
3-Trimethylsilyl-5-[N,N-1,1,4,4-tetramethyl-1,4-disilethylene)]aminobenzylalcohol To a solution of 3-trimethylsilyl-5-[N,N-(1,1,4,4-tetramethyl-1,4-disilethylene)]aminophenyl magnesium bromide prepared from 3-bromo-5-trimethylsilyl-N,N-(1,1,4,4-tetramethyl-1,4-disilethylene)aniline (11.26 g, 30 mmol) and magnesium (0.73 g, 30 mmol) in diethyl ether (60 ml) was added paraformaldehyde (0.99 g, 33 mmol). Then the mixture was refluxed 18 hours, cooled to 0° C. and treated with a saturated ammonium chloride solution (50 ml). The ether layer was separated, washed with water, brine, dried over $MgSO_4$ and concentrated. The title compound was recrystallized from diethyl ether-hexane.

Step D:
3-Trimethylsilyl-5-[N,N-1,1,4,4-tetramethyl-1,4-disilethyene)]aminobenzaldehyde The title compound was prepared as described in Step B of Example 5 and recrystallized from diethyl ether hexane.

Step E:
Ethyl-2,2-difluoro-3-hydroxy-3-[3-trimethylsilyl-5-[N,N-(1,1,4,4-tetramethyl-1,4-disilethylene)]amino]phenyl propionate The title compound was prepared as described in Step C of Example 5 and recrystallized from diethyl ether hexane.

Step F:
Ethyl-2,2-difluoro-3-acetoxy-3-(3-trimethylsilyl-5-amino) phenyl propionate To a solution of ethyl-2,2-difluoro-3-hydroxy-3-[3-trimethylsilyl-5-[N,N-(1,1,4,4-tetramethyl-1,4-disilethylene)]amino]phenyl propionate (5.51 g, 12 mmol) and triethylamine (1.31 g, 13 mmol) in tetrahydrofuran (15 ml) at 0° C. was added acetyl chloride (0.94 g, 12 mmol). Then the mixture was stirred 1 hour at room temperature, cooled to 0° C., treated slowly with 10% HCl in ethanol (20 ml) followed by stirring for 3 hours at room temperature. The solvents were removed under reduced pressure and the residue partitioned between diethyl ether and water. The acidic aqueous layer was separated and made basic, then extracted twice with diethyl ether. The organic extract was dried over $MgSO_4$ and concentrated and the product was purified by conversion to its hydrochloride salt.

Step G:
Ethyl-2,2-difluoro-3-acetoxy-3-(3-trimethylsilyl-5-nitrile) phenylpropionate To a solution of ethyl-2,2-difluoro-3-acetoxy-3-(3-trimethylsilyl-5-amino)phenyl propionate hydrochloride (3.96 g, 10 mmol) in 0.5N HCl (20 ml) at 0° C. was added a solution of sodium nitrite (0.69 g, 10 mmol) in water (5 ml), the temperature being kept at 0°–5° C. by the addition of cracked ice. Then the mixture was cautiously neutralized by adding dry sodium carbonate. The resulting mixture was added dropwise to a solution of copper cyanide (0.90 g, 10 mmol) in ice water (10 ml) and toluene (20 ml) while vigorous stirring was maintained and the temperature being kept at 0°–5° C. Then the temperature was held at 0°–5° C. for 30 min, allowed to rise to room temperature and stirring was continued for 3 hours. Then the toluene layer was separated, washed twice with water, brine, dried over $MgSO_4$ and concentrated under reduced pressure. The title compound was purified on silica gel (30% ethyl acetate in cyclohexane).

Step H:
2,2-Difluoro-3-hydroxy-3-(3-trimethylsilyl)-5-nitrile) phenylpropionic acid To a solution of ethyl-2,2-difluoro-3-acetoxy-3-(3-trimethylsilyl-5-nitrile)phenyl propionate (1.85 g, 5 mmol) in 1,2-dimethoxyethane (8 ml) and water (2 ml) was added lithium hydroxide (0.36 g, 15 mmol) and the mixture was stirred 2 hours at room temperature. Then the solvent was removed under reduced pressure. The crude product was dissolved in water (20 ml) and extracted twice with diethyl ether. Then the aqueous layer was made acidic with 1N HCl and extracted with dichloromethane. The organic layer was dried over $MgSO_4$ and concentrated under reduced pressure. The title compound was recrystallized from diethyl ether.

Step I:
2,2-Difluoro-3-keto-3-(3-trimethylsilyl-5-nitrile) phenylpropionic acid

The title compound was prepared as described in Step B of Example 5 and recrystallized from diethyl ether.

EXAMPLE 7

1,1,1-Trifluoro-3-(3-trimethylsilyl)phenylpropanone
Step A:
3-Trimethylsilylbenzylethyl ether To a solution of 3-trimethylsilylbenzylalcohol (3.60 g, 20 mmol) in tetrahydrofuran (40 ml) at 0° C. was added dropwise 1.5M butyllithium (13.3 ml) and the mixture was stirred for 10 minutes. Then iodobutane (3.12 g, 20 mmol) in tetrahydrofuran (20 ml) was added dropwise and the mixture was stirred at room temperature for 3 hours. The reaction mixture was treated with water (100 ml) and the crude product was extracted twice with diethyl ether (100 ml). The organic layer was washed with brine, dried over MgSO$_4$, concentrated and 3-trimethylsilylbenzylethyl ether was purified by distillation.
Step B:
1,1,1-Trifluoro-3-(3-trimethylsilyl)phenylpropanone To a suspension of lithium (0.42 g, 60 mmol) in tetrahydrofuran (10 ml) at −10° C. was added dropwise 3-trimethylsilylbenzylethyl ether (2.08 g, 10 mmol) in diethyl ether (10 ml). Then the mixture was allowed to react 1 hour at −10° C. and added dropwise to a solution of ethyl trifluoroacetate (2.84 g, 20 mmol) in diethyl ether (20 ml) at −78° C. Then the cooling bath was removed and the mixture was allowed to warm to room temperature, treated with 3N HCl (20 ml). The organic layer was separated, washed with water, brine, dried over MgSO$_4$ and concentrated under reduced pressure. Chromatography on silica gel (10% diethyl ether in cyclohexane), followed by distillation under reduced pressure, afforded the expected product.

EXAMPLE 8

1,1,1-Trifluoro-3-(3-trimethylsilyl-5-amino)phenylpropanone hydrochloride
Step A:
3-Trimethylsilyl-5-[N,N-(1,1,4,4-tetramethyl-1,4-disilethylene)]aminobenzylbromide To a solution of 3-bromo-5-trimethylsilyl-[N,N-(1,1,4,4-tetramethyl-1,4-disilethylene)aniline (3.86 g, 10 mmol) in diethyl ether (10 ml) at 0° C. was added 1.5M butyllithium (6.67 ml). Then the mixture was stirred 15 min, cooled to −78° C. and treated with dibromomethane (1.74 g, 10 mmol) in diethyl ether (5 ml). Stirring was continued 30 min at −78° C., then the temperature was allowed to rise to room temperature and stirring was continued for 1 hour. To the mixture was added a saturated ammonium chloride solution (20 ml) and the organic layer separated, washed with water, brine, dried over MgSO$_4$ and concentrated under reduced pressure. The title compound was purified by recrystallization from hexane.
Step B:
1,1,1-Trifluoro-3-(3-trimethylsilyl-5-amino)phenylpropanone hydrochloride To a solution of 3-trimethylsilyl-5-[N,N-(1,1,4,4-tetramethyl-1,4-disilethylene)]aminobenzyl magnesium bromide prepared from 3-trimethylsilyl-5-[N,N-(1,1,4,4-tetramethyl-1,4-disilethylene)]aminobenzylbromide (2.00 g, 5 mmol) and magnesium (0.12 g, 5 mmol) in diethyl ether (10 ml) at −78° C. was added ethyltrifluoroacetate (1.42 g, 10 mmol) over 5 min. Then the cooling bath was removed and the mixture was allowed to warm to 0° C., treated slowly with 10% HCl in ethanol (10 ml), followed by stirring for 3 hours at room temperature. The solvents were removed under reduced pressure and the residue partitioned between diethyl ether and water. The acidic aqueous layer was separated and made basic, then extracted twice with diethyl ether. The ether extract was dried over MgSO$_4$ and concentrated and the title compound was purified by conversion to its HCl salt.

EXAMPLE 9

Ethyl-2,2-difluoro-3-keto-4-(3-trimethylsilyl)phenyl butanoate
Step A:
3-Trimethylsilylbenzylbromide A mixture of 3-trimethylsilyltoluene (3.28 g, 10 mmol), N-bromosuccinimide (1.78 g, 10 mmol) and benzoylperoxide (10 mg) in CCl$_4$ (20 ml) was stirred under reflux for 3 hours, then cooled and filtered. The solvent was removed under reduced pressure and 3-trimethylsilylbenzylbromide was purified by distillation.
Step B:
2-(3-Trimethylsilyl)phenylethanol The title compound was prepared as described in Step C of Example 6 and recrystallized from diethyl ether-hexane.
Step C:
2-(3-Trimethylsilyl)phenylethanal The title compound was prepared as described in Step B of Example 5 and purified by distillation.
Step D:
Ethyl-2,2-difluoro-3-hydroxy-4-(3-trimethylsilyl)phenyl butanoate The title compound was prepared as described in Step C of Example 5.
Step E:
Ethyl-2,2-difluoro-3-keto-4-(3-trimethylsilyl)phenyl butanoate The title compound was prepared as described in Step B of Example 5 and purified by distillation.

EXAMPLE 10

Ethyl-2,2-difluoro-3-keto-4-(3-trimethylsilyl-5-amino)phenyl butanoate hydrochloride
Step A:
2-[3-Trimethylsilyl-5-[N,N-(1,1,4,4-tetramethyl-1,4-disilethylene)amino]]phenyl ethanol The title compound was prepared as described in Step C of Example 6.
Step B:
2-[3-Trimethylsilyl-5-[N,N-(1,1,4,4-tetramethyl-1,4-disilethylene)amino]]phenyl ethanal The title compound was prepared as described in Step B of Example 5.
Step C:
Ethyl-2,2-difluoro-3-hydroxy-4-[3-trimethylsilyl-5-[N,N-(1,1,4,4-tetramethyl-1,4-disilethylene)amino]]phenyl butanoate The title compound was prepared as described in Step C of Example 5.
Step D:
Ethyl-2,2-difluoro-3-keto-4-(3-trimethylsilyl-5-amino)phenyl butanoate hydrochloride The title compound was prepared by following the procedure described in Step B of Example 5 and purified to its hydrochloride salt by removing the protecting amino group with 10% HCl in ethanol.

EXAMPLE 11

1,1,1-Trifluoro-2-(3-trimethylsilylmethyl)phenyl ethanone
Step A:
3-Trimethylsilylmethylphenylbromide The title compound was prepared as described in Step A of Example 1.

Step B:
1,1,1-Trifluoro-2-(3-trimethylsilylmethyl)phenyl ethanone

The title compound was prepared as described in Step B of Example 1.

EXAMPLE 12

1,1,1-Trifluoro-2-(3-trimethylsilylmethyl-5-amino)phenyl ethanone hydrochloride
Step A:
3-Trimethylsilylmethyl-5-[N,N-(1,1,4,4-tetramethyl-1,4-disilethylene]amino phenylbromide To a solution of 3,5-dibromo-N,N-(1,1,4,4-tetramethyl-1,4-disilethylene)aniline (7.86 g, 20 mmol) in diethyl ether (20 ml) at 0° C. was added 1.5M butyllithium in hexane (13.3 ml) over 10 min. Then the mixture was stirred 15 min at 0° C. and iodomethyltrimethylsilane (4.28 g, 20 mmol) in diethyl ether (10 ml) was added dropwise. The mixture was stirred 3 hours at room temperature and treated with a saturated ammonium chloride solution (20 ml). The ether layer was separated, washed with water, brine, dried over MgSO$_4$ and concentrated under reduced pressure. The title compound was recrystallized from hexane.
Step B:
1,1,1-Trifluoro-2-(3-trimethylsilylmethyl-5-amino)phenyl ethanone hydrochloride The title compound was prepared by following the procedure described in Step B of Example 1. After hydrolysis and removing of the organic layer, the aqueous layer was made basic and extracted twice with dichloromethane. The dichloromethane extract was dried over MgSO$_4$, concentrated under reduced pressure and the title compound was purified by conversion to its hydrochloride salt.

EXAMPLE 13

Ethyl-2,2-difluoro-3-keto-3-(3-trimethylsilylmethyl)phenyl propionate
Step A:
3-Trimethylsilylmethylbenzylalcohol To a solution of 3-methylbenzylalcohol (6.10 g, 50 mmol) in anhydrous diglyme (200 ml) at −78° C. was added 1.5M butyllithium (100 ml) over 20 min. The resulting mixture was allowed to warm to −20° C. and stirred for 30 min. Then a mixture of trimethylchlorosilane (19.0 g, 175.0 mmol) and triethylamine (5.05 g, 50 mmol) was added and the final solution was stirred at room temperature for 3 hours. The reaction mixture was treated with ice water (200 ml), extracted three times with diethyl ether (100 ml) and the extracts washed twice with water, brine, dried over MgSO$_4$ and concentrated. The crude product was dissolved in 90% aqueous methanol (200 ml) and refluxed for 1 hour. Then the solvents were removed and 3-trimethylsilylmethylbenzylalcohol was purified by fractional distillation.
Step B:
3-Trimethylsilylmethylbenzaldehyde The title compound was prepared as described in Step B of Example 5.
Step C:
Ethyl-2,2-difluoro-3-hydroxy-3-(3-trimethylsilylmethyl) phenyl propionate The title compound was prepared as described in Step C of Example 5.
Step D:
Ethyl-2,2-difluoro-3-keto-3-(3-trimethylsilylmethyl)phenyl propionate The title compound was prepared as described in Step B of Example 5.

EXAMPLE 14

Ethyl-2,2-difluoro-3-keto-3-(3-trimethylsilylmethyl-5-amino) phenyl propionate hydrochloride
Step A:
3-Bromo-5-[N,N(1,1,4,4-tetramethyl-1,4-disilethylene) amino]toluene To a solution of 3,5-dibromo-N,N-(1,1,4,4-tetramethyl-1,4-disilethylene)aniline (19.65 g, 50 mmol) in diethyl ether (50 ml) at 0° C. was added 1.5M butyllithium (33.3 ml) over 15 min. Then the mixture was stirred for 15 min and iodomethane (7.10 g, 50 mmol) in diethyl ether (15 ml) was added over 15 min at 0° C. The mixture was stirred 1 hour at 0° C. and was allowed to warm to room temperature and stirred for 3 hours. Then the reaction mixture was poured into ice water (100 ml). The organic layer was separated, washed with brine, dried over MgSO$_4$ and concentrated. The title compound was recrystallized from hexane.
Step B:
3-Methyl-5-[N,N(1,1,4,4-tetramethyl-1,4-disilethylene)] aminobenzyl alcohol The title compound was prepared as described in Step C of Example 6.
Step C:
3-Trimethylsilylmethyl-5-[N,N(1,1,4,4-tetramethyl-1,4-disilethylene)]aminobenzyl alcohol The title compound was prepared as described in Step A of Example 13 and recrystallized from hexane.
Step D:
3-Trimethylsilylmethyl-5-[N,N(1,1,4,4-tetramethyl-1,4-disilethylene)]aminobenzaldehyde The title compound was prepared as described in Step D of Example 6.
Step E:
Ethyl-2,2-difluoro-3-hydroxy-3-[3-trimethylsilylmethyl-5-[N,N-(1,1,4,4-tetramethyl-1,4-disilethylene)]amino] phenylpropionate The title compound was prepared as described in Step E of Example 6.
Step F:
Ethyl-2,2-difluoro-3-keto-3-(3-trimethylsilylmethyl-5-amino)phenyl propionate hydrochloride The title compound was prepared as described in Step D of Example 10.

EXAMPLE 15

Preparation of 3,3,3,2,2-Pentafluoro-2-(3-trimethylsilylphenyl)propanone
Step A:
Preparation of N-Methoxy-N-methyl-3-trimethylsilylbenzamide A solution of 3-trimethylsilylbenzoic acid in methylene chloride (12 ml) was cooled to −22° C. and N-methylmorpholine (2.0 ml) was added. To the mixture isobutylchloroformate (0.88 ml) was added. The mixture was stirred for 25 min. followed by the addition of N,O-dimethylhydroxylamine hydrochloride (0.9 g). The mixture was stirred at −22° C. for 1 hr., allowed to warm to room temperature and stirred for 1.5 hr. The reaction mixture was poured into dil HCl and the aqueous phase was extracted with diethyl ether (2×100 ml). The combined organic extracts were washed with dil NaHCO$_3$ and dried over Na$_2$SO$_4$. The solvent was removed in vacuo and the crude product purified by flash chromatography (10% EtOAc in hexane) to yield 600 mg of the desired product. HRMS calc. 238.1263. Found: 238.1268.

Step B:
Preparation of 3,3,3,2,2-Pentafluoro-2-(3-trimethylsilylphenyl)propanone A solution of N-methoxy-N-methyl-3-trimethylsilylbenzamide (325 mg) in diethyl ether (25 ml) was cooled to −78° C. and pentafluoroethyliodide (2.25 ml) was added. To the mixture methyllithium-lithiumbromide complex (9.0 ml of a 1.5M solution in diethyl ether) was added. The reaction mixture was allowed to stir at −78° C. for 5 min, allowed to warm to 0° C. and poured into dil HCl. The aqueous phase was extracted with diethyl ether (2×75 ml) and the combined organic extracts were washed with dil $NaHCO_3$ and dried over $Na_2SO_4$. The removal of solvent in vacuo yielded 385 mg of crude product. The product was purified by flash chromatography (20% ethyl acetate in hexane) to yield 325 mg of the desired product. HRMS calc 297.0734. Found: 297.0743.

EXAMPLE 16

Preparation of 1-(3-(trimethylsilyl)phenyl propan-1,2-dione 0.75 g of Ethyl vinyl ether (10.4 mmol) was added to 8.0 ml of THF and the mixture cooled to −78° C. 6.3 ml of 1.7M t-butyllithium (10.7 mmol) in pentane was added. The mixture was warmed to −5° C. and stirred for 1.2 hours. The mixture was recooled to −78° C. and 0.60 g of N-methoxy-N-methyl-3-trimethylsilylbenzamide in 3 ml of THF was added. The mixture was stirred for 10 min, quenched into dil HCl and extracted with diethyl ether. The combined extracts were washed with $NaHCO_3$, dried over $Na_2SO_4$ and solvent was removed in vacuo. The crude product was dissolved in 50 ml of THF which contains 1% $H_2O$ and 0.2 ml of concentracted HCl was added. The mixture was stirred for 2½ hours at room temperature, poured in dil $NaHCO_3$ and extracted with diethyl ether. The combined extracts were dried over $Na_2SO_4$. The solvent was removed in vacuo and the crude product chromatographed on silica gel with 10% EtOAc/hexane, yield 250 mg. Further purification was performed by dissolving the product in 50 ml of THF and 0.5 ml of $H_2O$ and 0.2 ml of concentrated HCl were added. The mixture was stirred for 2 hours, poured into dil. $NaHCO_3$ and extracted with diethyl ether. The combined extracts were dried over $Na_2SO_4$ and removal of solvent gave 200 mg. The product was distilled (bulb to bulb at less than 10 mmHg). Obtained 170 mg. The crude product was finally purified by loading onto silica gel and the product was eluted with 10% EtOAc/hexane to yield 120 mg.

EXAMPLE 17

Evaluation of 2,2,2-Trifluoro-1-(3-trisilylpenyl)ethanone for Transdermal Delivery and Demonstraton of Prototype Transdermal Delivery Systems An in vitro excised hairless mouse skin/modified Franz Diffusion Cell model was used to evaluate skin permeability of neat MDL 73,745, the title compound of Example 1, and permeation profile of MDL 73,745 from various prototype transdermal delivery systems. Prototype transdermal delivery systems containing MDL 73,745 were prepared in various acrylic, silastic, ethylene vinyl acetate copolymer, and rubber based pressure sensitive adhesives and evaluated in the in vitro skin permeation cell model. In vitro skin permeation rates from these prototypes varied between 7.38 and 68.87 μg/cm²/hr.

In vitro skin permeation model: For this study an in vitro finite-dose glass diffusion cell (modified Franz Diffusion Cell)/freshly excised hairless mouse skin model was used. The diffusion consists of two parts: (i) a receptor compartment which is an upright reservoir jacketed by a glass chamber on the outside. Experiments were conducted at 37° C. by circulating thermostatically controlled water at 37° C. in this jacket and (ii) donor cap, which is clamped together with the receptor compartment with a metal clamp. A piece of skin/(transdermal formulation) is sandwiched between the donor and the receptor compartments and clamped together. Sampling from the receptor compartment is taken at predetermined time intervals through the sampling port.

Hairless mouse: Outbred Nude mouse {CRL NU/NU (CD1) BR, 6–8 weeks old, male} from Charles River, Mass.

Excised skin: Immediately following sacrifice by $CO_2$ gas, a portion (3.5×3.5 cm) of the full-thickness abdominal skin was carefully excised from the hairless mouse. The dermal side of the skin was carefully cleaned of any adhering subcutaneous tissue and/or blood vessels. Extreme care was taken not to scratch or damage the stratum corneum. Before mounting onto the diffusion cell, each piece of skin was carefully inspected to insure that the skin was not damaged.

Dermal elution media: A 5% solution of polyethylene glycol 20 Oleyl ether (Trycol®, Emery) in 0.9% sodium chloride was used as the receptor medium for the modified Franz Diffusion Cells. Trycol® increases the aqueous solubility of MDL 73,745 which helps maintain a sink condition in the receptor side of the diffusion cells. In a previously published study (R. L. Bronaugh and R. F. Stewart, *J. Pharm. Sci.*, Vol. 73, No. 9, 1984, p. 1255) PEG 20 oleyl ether was not found to affect the integrity or the permeation characteristics of the skin. Temperature of the dermal elution media was maintained at 37° C. using a thermostated constant temperature circulating water bath.

Laminates for prototype transdermal delivery systems: Device components from 3M Corp. (St. Paul, Minn.) were used in making prototype transdermal delivery systems for MDL 73,745. 3M product #1109 (a skin toned, aluminized polyester laminate) served as the substrate film; 3M product #1022 (a fluoropolymer coated polyester film) served as the 'release' liner.

Adhesives used in formulating prototype transdermal delivery systems: Pressure Sensitive Adhesives (PSA) from a variety of sources were used in formulating various prototype transdermal delivery systems containing MDL 73,745. Adhesives evaluated were as follows:

| # | Adhesive Name | Adhesive Type | Adhesive Supplier |
|---|---|---|---|
| 1 | DuroTak 80-1054 | Polyacrylate solution | National Starch & Chemical Co. |
| 2 | DuroTak 80-1058 | Polyacrylate solution | National Starch & Chemical Co. |
| 3 | DuroTak 80-1074 | Polyacrylate solution | National Starch & Chemical Co. |
| 4 | DuroTak 80-1194 | Polyacrylate solution | National Starch & Chemical Co. |
| 5 | DuroTak 80-9511 | Polyacrylate solution | National Starch & Chemical Co. |
| 6 | DuroTak 72-9676 | Polyacrylate solution | National Starch & Chemical Co. |
| 7 | DuroTak 72-9852 | Polyacrylate solution | National Starch & Chemical Co. |
| 8 | Gelva 737 | Polyacrylate solution | Monsanto |
| 9 | Gelva 788 | Polyacrylate solution | Monsanto |
| 10 | Product #9871 | Polyacrylate solution | 3M Corp. |
| 11 | Nacor 38-4515 | Polyacrylate solution | National Starch & Chemical Co. |

| #  | Adhesive Name     | Adhesive Type                              | Adhesive Supplier             |
|----|-------------------|--------------------------------------------|-------------------------------|
| 12 | BioPSA X7-4202    | Silicone PSA                               | Dow Corning Corp.             |
| 13 | BioPSA X7-4402    | Silicone PSA                               | Dow Corning Corp.             |
| 14 | BioPSA X7-4502    | Silicone PSA                               | Dow Corning Corp.             |
| 15 | DuroTak 72-9718   | Rubber based PSA                           | National Starch & Chemical Co.|
| 16 | Eva-Tak 72-9660   | Ethylene Vinyl Acetate copolymer emulsion PSA | National Starch & Chemical Co. |

Skin permeation profile from neat MDL 73,745 and from Prototype formulations: Full-thickness skin, prepared freshly as outlined above, was mounted in a modified Franz Diffusion Cell with the stratum corneum side facing upward. To study the permeation profile of neat MDL 73,745, 50 µl of MDL 73,745 was uniformly applied onto the stratum corneum. The donor cap was placed over the skin and the whole assembly was then securely clamped together. The donor cap was covered with a piece of aluminum foil to reduce the volatilization of MDL 73,745. To evaluate the skin permeation profile of MDL 73,745 from a prototype transdermal formulation, a unit of prototype transdermal system (about 4.9 cm² circular) containing MDL 73,745 was placed onto the skin with the drug releasing side in intimate contact with the stratum corneum (slight pressure was applied to insure good contact). The donor cap was placed over the skin and the whole assembly was then securely clamped together.

Dermal elution medium (5% w/w Trycol® in normal saline) was then introduced into the receptor compartment through the sampling port. At predetermined time intervals, the entire volume of the receptor solution was withdrawn and immediately replaced with the same volume of fresh, drug free dermal elution medium (5% w/w Trycol® in normal saline), maintained at 37° C. The concentration of MDL 73,745 was determined by a sensitive HPLC method described under Analytical Method section below.

Analytical Method: An automated high performance liquid chromatograph equipped with a gradient pump (Waters Model 600E), autoinjector/sampler (Waters, Model 715 WISP), and a variable wavelength UV detector (Waters, Model 490) was used. The autoinjector/sampler was maintained at 2° C. to reduce possible evaporation/degradation of MDL 73,745 in the sample.

HPLC conditions for the analysis of MDL 73,745 in samples from skin permeation experiments (i.e., 5% Trycol® in normal saline) were as follows:

```
Column:      Zorbax, Rx—C18, 4.0 × 80 mm, 5 µm (Reliance Cartridge),
             @ RT.
Mobil Phase: Gradient conditions were as follows:
   Initial:    10% A + 90% C      @ 1 ml/min.
   @ 3 min:    100% B             @ 1 ml/min.
   @ 5 min:    10% A + 90% C      @ 1 ml/min.
```

A: Water
B: Acetonitrile
C: 50/50 water/acetonitrile, 0.25% triethylamine, pH adjusted to 3 with 50% phosphoric acid/water.
Run time: 12 minutes
Detection Wavelength: 210 nm.

Under above chromatographic conditions, MDL 73,745 eluted at approximately 4.9 minutes.

Method of preparation of prototypes: The required amount of MDL 73,745 was added to a selected adhesive and the mixture was stirred until a uniform solution resulted. A 200 µm (or as specified in the text) film of this mixture was coated onto 3M laminate #1022 (polyester coated with a fluoropolymer release liner) using a hand coater. This film was dried in a vacuum oven at 50° C. for 10 minutes (vacuum was on for 7 minutes and then purged for the next 3 minutes). NOTE: curing conditions (temp. and time) for some of the prototypes were slightly different. The substrate (3M #1109) was laminated onto this dried film using a mechanical laminator.

To prepare prototypes in the water based emulsion adhesives, the adhesive/drug mixture was coated on the substrate layer (3M #1109) instead of on the release liner. Because of surface tension, water based adhesive mixture could not be coated directly onto the release liner. This coated film was then dried at 80° C. for 10 minutes in a forced circulation oven. The release liner (3M #1022) was then laminated onto the dried film.

Measurement of Tack: The following conditions were used for the measurement of 'Tack' for various prototype formulations:

Equipment: Polyken Probe Tack Tester
Probe Diameter: 5 mm (Area: 0.19635 cm2)
Probe: 304 Stainless Steel @37° C.;
Wt. of Annular ring: 19.42 gm (or 98.90 g./cm² of pressure on the probe tip)
Speed: 0.1 cm/sec.;
Dwell time: 5.0 seconds;
Mode: Track
Chart Recorder: 0.5 volts full scale (100 gms=1 volt).

Prototype Transdermal Delivery Systems of MDL 73,745: The following prototype formulations containing various drug loading were prepared for evaluation in the present study:

1. 50–80% w/w MDL 73,745 in DuroTak 80-1074 pressure sensitive acrylic adhesive (National Starch & Chemical Company).
2. 50–70% w/w MDL 73,745 in DuroTak 80-9511 pressure sensitive acrylic adhesive (National Starch & Chemical Company).
3. 50–80% w/w MDL 73,745 in DuroTak 72-9676 pressure sensitive acrylic adhesive (National Starch & Chemical Company).
4. 50–80% w/w MDL 73,745 in DuroTak 80-1194 pressure sensitive acrylic adhesive (National Starch & Chemical Company). 5. 50–70% w/w MDL 73,745 in DuroTak 80-1054 pressure sensitive acrylic adhesive (National Starch & Chemical Company). 6. 50, 60% w/w MDL 73,745 in DuroTak 80-1058 pressure sensitive acrylic adhesive (National Starch & Chemical Company). 7. 70, 80% w/w MDL 73,745 in DuroTak 72-9852 pressure sensitive acrylic adhesive (National Starch & Chemical Company). 8. 50–70% w/w MDL 73,745 in acrylic pressure sensitive adhesive #737 (Monsanto). 9. 50–70% w/w MDL 73,745 in acrylic pressure sensitive adhesive #788 (Monsanto). 10. 50–60% w/w MDL 73,745 in acrylic pressure sensitive adhesive #9871 (3M Corp.). 11. 50% w/w MDL 73,745 in Nacor 38-4515 emulsion acrylic pressure sensitive adhesive (National Starch & Chemical Company). 12. 50% w/w MDL 73,745 in Eva-Tak 72-9660 emulsion Ethylene vinyl acetate copolymer pressure sensitive adhesive (National Starch & Chemical Company). 13. 20% w/w MDL 73,745 in DuroTak 72-9718 rubber-based pressure sensitive adhesive (National Starch & Chemical Company). 14. 20, 30% w/w MDL 73,745 in X7-4202 Silicone pressure sensitive adhesive (Dow Corning). 15. 20, 30% w/w MDL 73,745 X7-4402 Silicone pressure sensitive adhesive (Dow Corning). 16. 20, 30% w/w MDL 73,745 X7-4502 Silicone pressure sensitive adhesive (Dow Corning).

RESULTS AND DISCUSSION

Skin permeation profile of neat MDL 73,745:

Results indicate that neat MDL 73,745 transports through excised hairless mouse skin in a controlled zero order fashion and the rate of transdermal delivery is 208.21 µg/cm$^2$/hr (FIG. 1). Because of MDL 73,745 'Activity' of one at the neat (Pure) form, this would be the highest possible rate of transdermal delivery of MDL 73,745 according to Fick's rule of passive diffusion through any barrier membrane.

Skin permeation profile of MDL 73,745 from various prototype formulations:

FIGS. 2 through 8 and Table 1 show the transdermal permeation profile of MDL 73,745 from prototype transdermal formulations in various acrylic pressure sensitive adhesives (PSA). Results indicate that MDL 73,745 can be successfully delivered in a controlled, zero-order fashion over a period of at least 24 hours. The rate of transdermal delivery of MDL 73,745 varied from 14.42 to 68.87 µg/cm$^2$/hr from prototype formulations containing 50 to 80% w/w in the adhesive solids. Prototypes containing MDL 73,745 loading higher than 80% were not viable because greater loading would plasticize the adhesive and increase its fluidity significantly which leads to pronounced deterioration of the physical integrity of the drug/adhesive matrix. The maximum loading of MDL 73,745 a particular adhesive could 'tolerate' without getting significantly plasticized depends upon that adhesive (specifically more likely on the molecular weight and the cross linking of that adhesive polymer). Results also clearly indicate that the rate of transdermal delivery can be effectively controlled by changing the drug loading in the adhesive matrix.

FIG. 9 and Table 1 show transdermal delivery of MDL 73,745 from a prototype prepared in an ethylene vinyl acetate copolymer pressure sensitive adhesive (Eva-Tak 72-9660, a water-borne emulsion type PSA). The rate of transdermal delivery varied from 33.86 to 47.15 mg/cm$^2$/hr from prototypes containing 50 to 70% w/w MDL 73,745 in the adhesive solids. As before, MDL 73,745 was delivered in a controlled, zero-order fashion throughout the duration of patch application and the rate of transdermal delivery can be controlled by controlling the drug loading. Lower delivery rate from prototypes containing 60% drug (20.59 µg/cm$^2$/hr) as compared to prototypes containing 50% drug (33.86 µg/cm$^2$/hr) could not be explained.

FIG. 10 and Table 1 show the transdermal delivery profile of MDL 73,745 from a prototype transdermal patch prepared in a water-borne emulsion type acrylic pressure sensitive adhesive (Nacor 38-4515). The rate of transdermal delivery of MDL 73,745 from prototypes containing 50% w/w drug was 19.18 µg/cm$^2$/hr. By comparing the delivery rates from other prototype formulatrions containing similar drug loading, it is obvious that this prototype delivers MDL 73,745 at a relatively lower rate through the excised hairless mouse skin. Relatively lower rate of transdermal delivery from this formulation may possibly be due to less favorable partitioning of MDL 73,745 between the adhesive polymer and the stratum corneum layer of the skin. Formulations containing higher loadings were not feasible as at higher drug loadings the acrylic polymer in this emulsion system would coalesce resulting in 'cracking' of the emulsion system.

Skin permeation profiles of MDL 73,745 from prototypes prepared in acrylic PSA supplied by 3M Corp. (Acrylic adhesive #9871) are shown in FIG. 11 and Table 1. Here again, the transdermal delivery of MDL 73,745 follows a constant, zero-order profile and the rate of transdermal delivery can be controlled by altering the drug loading in the adhesive matrix. Rates of transdermal delivery of MDL 73,745 were 13.01 and 21.04 µg/cm$^2$/hr from formulations containing 50 and 60% w/w drug loading, respectively. Formulations containing greater than 60% w/w MDL 73,745 could not be prepared as this caused significant plasticization (increase in the fluidity of the drug/adhesive matrix) of the adhesive matrix and thus the loss of proper physical integrity and the tack.

FIG. 12 and Table 1 show the skin permeation profile of MDL 73,745 from prototype formulations prepared in acrylic PSAs supplied by Monsanto. At 50% w/w drug loading the skin permeation rates were 8.63 and 12.95 µg/cm$^2$/hr from prototypes in Gelva 788 and Gelva 737, respectively. Prototypes containing higher drug loadings were not feasible due to plasticization and the resultant deterioration of tack of the drug/adhesive matrix.

Prototypes were also successfully formulated in Silicone pressure sensitive adhesives. FIG. 13 and Table 1 show the skin permeation profiles of MDL 73,745 from prototypes prepared in three silicone pressure sensitive adhesives: BioPSAs X7-4202, X7-4402, and X7-4502 (Dow Corning). Formulations containing higher than 30% drug loading could not be prepared due to plasticization of the adhesive matrix. In these adhesives, the rate of transdermal delivery varied from 7.38 to 24.71 µg/cm$^2$/hr from prototypes containing 20 and 30% w/w drug loading. It appears that the rates of transdermal delivery from these silicone PSA prototypes containing a particular drug loading are higher than from prototypes in acrylic or rubber based PSA containing comparable drug loading. Prototypes in acrylic PSA can produce higher rates of transdermal delivery because MDL 73,745 can be incorporated at a higher level in the acrylic PSA (prototype containing 80% w/w MDL 73,745 in Duro-Tak 72-9852 acrylic adhesive produced a rate of 68.87 µg/cm$^2$/hr).

The skin permeation profile of MDL 73,745 from prototype formulations prepared in rubber based (polyisobutylene) pressure sensitive adhesive (DuroTak 72-9718, National Starch & Chemical Company) is shown in FIG. 14. As in the case of prototype formulations of acrylic and silicone PSAs, skin permeation of MDL 73,745 follows a constant, zero-order profile. The rate of transdermal delivery from prototype formulations containing 20% w/w drug loading was 12.92 µg/cm$^2$/hr. Formulations containing higher drug loading could not be prepared as this caused plasticization and the resultant deterioration of tack of the adhesive matrix.

Tack of various prototypes: Table 1 shows the 'Tack' of various prototype formulations containing MDL 73,745. Table 2 shows the 'Tack' of some of the marketed transdermal products measured under identical experimental conditions. As is obvious from these observations, the tack of most of the prototype transdermal delivery systems are well within the range of all the currently marketed transdermal formulations. This indicates that these prototype formulations should presumably have good 'tack' to adhere to the skin for an expended period of transdermal application.

TABLE 1

In vitro skin permeation rates and "tack" from various prototype transdermal delivery systems of MDL 73,745

| # | Prototype Description | Total Tack ± SD (gms); n = 5 | Tack/cm² ± SD (gm/cm²) | Skin Permeation (μg/cm²/hr) ± SD; n = 3 |
|---|---|---|---|---|
| | Acrylic Pressure Sensitive Adhesives | | | |
| 1 | 50% w/w in DuroTak 80-1074 | 320.2 ± 28.25 | 1630.76 ± 143.87 | 14.42 ± 2.83 |
| 2 | 60% w/w in DuroTak 80-1074 | 221.6 ± 74.68 | 1128.60 ± 380.34 | 31.12 ± 4.28 |
| 3 | 70% w/w in DuroTak 80-1074 | 207.4 ± 68.69 | 1056.58 ± 349.83 | 34.25 ± 10.25 |
| 4* | 80% w/w in DuroTak 80-1074 | NP | NP | 46.14 ± 12.28 |
| 5 | 50% w/w in DuroTak 80-1058 | 98.0 ± 32.90 | 499.11 ± 167.56 | 22.69 ± 4.05 |
| 6 | 60% w/w in DuroTak 80-1058 | 89.0 ± 17.82 | 453.27 ± 90.76 | 26.02 ± 4.17 |
| 7 | 50% w/w in DuroTak 80-9511 | 50.8 ± 13.66 | 258.72 ± 69.57 | 15.77 ± 4.39 |
| 8 | 60% w/w in DuroTak 80-9511 | 23.3 ± 9.04 | 118.16 ± 46.04 | 29.74 ± 2.20 |
| 9 | 70% w/w in DuroTak 80-9511 | 8.4 ± 0.89 | 42.78 ± 4.53 | 35.28 ± 15.46 |
| 10 | 50% w/w in DuroTak 72-9676 | 143.6 ± 9.56 | 731.35 ± 48.69 | 19.31 ± 3.98 |
| 11 | 60% w/w in DuroTak 72-9676 | 66.6 ± 35.46 | 339.19 ± 180.60 | 28.65 ± 1.83 |
| 12 | 70% w/w in DuroTak 72-9676 | 45.8 ± 19.18 | 233.26 ± 97.68 | 35.65 ± 2.19 |
| 13 | 80% w/w in DuroTak 72-9676 | 12.8 ± 8.70 | 65.19 ± 44.31 | 56.47 ± 19.42 |
| 14 | 50% w/w in DuroTak 80-1194 | 277.8 ± 24.71 | 1414.82 ± 125.85 | 17.83 ± 3.41 |
| 15 | 60% w/w in DuroTak 80-1194 | 91.6 ± 26.26 | 466.51 ± 133.74 | 30.03 ± 5.33 |
| 16 | 70% w/w in DuroTak 80-1194 | 14.6 ± 8.85 | 74.36 ± 45.07 | NA |
| 17 | 80% w/w in DuroTak 80-1194 | 4.8 ± 2.05 | 24.45 ± 10.44 | NA |
| 18 | 50% w/w in DuroTak 80-1054 | 170.8 ± 25.90 | 869.87 ± 131.91 | 24.99 ± 6.28 |
| 19 | 60% w/w in DuroTak 80-1054 | 80.6 ± 47.08 | 410.49 ± 239.76 | 24.10 ± 8.90 |
| 20 | 70% w/w in DuroTak 80-1054 | 30.8 ± 12.34 | 156.86 ± 62.85 | NA |
| 21* | 50% w/w in Monsanto 737 | NP | NP | 8.63 ± 2.39 |
| 22* | 60% w/w in Monsanto 737 | 23.8 ± 6.42 | 121.21 ± 32.70 | NA |
| 23* | 70% w/w in Monsanto 737 | 14.4 ± 2.19 | 73.34 ± 11.15 | NA |
| 24* | 50% w/w in Monsanto 788 | 45.2 ± 22.49 | 230.20 ± 114.54 | 12.95 ± 2.64 |
| 25* | 60% w/w in Monsanto 788 | 15.8 ± 8.61 | 80.47 ± 43.85 | NA |
| 26* | 70% w/w in Monsanto 788 | 8.67 ± 8.64 | 44.45 ± 44.00 | NA |
| 27* | 50% w/w in 3M 9871 | 136.8 ± 25.01 | 696.71 ± 127.37 | 13.01 ± 3.09 |
| 28* | 60% w/w in 3M 9871 | 55.2 ± 8.26 | 281.13 ± 42.07 | 21.04 ± 7.22 |
| | Water Based Adhesives (Emulsions) | | | |
| 29 | 50% w/w in Eva-Tak 72-9660 | 41.2 ± 9.09 | 209.83 ± 46.29 | 32.85 ± 8.39 |
| 30 | 50% w/w in Nacor 38-4515 | 26.60 ± 3.85 | 135.47 ± 19.61 | 19.18 ± 4.14 |
| | Silicone PSA (Dow Corning) | | | |
| 31* | 20% w/w in X7-4202 | 117.6 ± 48.18 | 598.93 ± 245.38 | 16.48 ± 1.57 |
| 32 | 30% w/w in X7-4202 | 19.8 ± 10.92 | 100.84 ± 55.61 | 19.26 ± 8.77 |
| 33* | 20% w/w in X7-4402 | 308.0 ± 68.87 | 1568.63 ± 350.75 | 7.38 ± 1.08 |
| 34 | 30% w/w in X7-4402 | 22.2 ± 6.3 | 113.06 ± 32.08 | 24.70 ± 7.16 |
| 35* | 20% w/w in X7-4502 | 418.4 ± 59.82 | 2130.89 ± 304.66 | 8.69 ± 5.07 |
| 36 | 30% w/w in X7-4502 | 75.4 ± 98.20 | 384.00 ± 500.13 | 24.71 ± 9.00 |
| | Rubber Based PSA | | | |
| 37 | 20% w/w in DuroTak 72-9718 | 236.6 ± 105.92 | 1204.99 ± 539.44 | 12.92 ± 1.79 |
| 38 | 30% w/w in DuroTak 72-9718 | 121.0 ± 48.02 | 616.25 ± 244.56 | NA |

*Patches cured at 100° C. for 5 minutes. All other patches were cured at 50° C. for 10 minutes.
NP: Test Not Performed.
NA: Data not available. Skin permeation study was not done; the adhesive was significantly plasticized because of high drug loading.

TABLE 2

Tack of some marketed Therapeutic Transdermal Delivery Systems

| # | Product Description | Total Tack ± SD (gms) | Tack/cm² ± SD (gm/cm²) |
|---|---|---|---|
| 1 | Catapres TTS-3 (Clonidine) 0.3 mg/day; 7 days; Bl | 144.0 ± 35.0 | 733.38 ± 178.25 |
| 2 | Transderm-Nitro-5; 10 cm² (5 mg/day; 1 day); Ciba-Geigy | 211.6 ± 41.7 | 1077.67 ± 212.37 |
| 3 | Transderm-Nitro-10; 20 cm² (10 mg/day; 1 day); Ciba-Geigy | 176.2 ± 107.92 | 897.38 ± 549.63 |
| 4 | Nitro-Dur II; 10 cm²; (5 mg/day; 1 day); Schering Plough | 103.2 ± 89.01 | 525.59 ± 453.32 |
| 5 | Nitro-Dur II; 20 cm²; (10 mg/day; 1 day); Schering Plough | 239.4 ± 63.06 | 1214.16 ± 321.16 |
| 6 | Deponit; 32 cm² (10 mg/day; 1 day); Wyeth/Lohymann | 200.4 ± 182.81 | 1020.63 ± 931.04 |

TABLE 2-continued

Tack of some marketed Therapeutic Transdermal Delivery Systems

| # | Product Description | Total Tack ± SD (gms) | Tack/cm² ± SD (gm/cm²) |
|---|---|---|---|
| 7 | Estraderm 0.05; 10 cm² (0.05 mg/day; 3 days); Ciba-Geigy | 9.6 ± 6.43 | 48.89 ± 32.75 |
| 8 | OpSite Dressing (Smith Nephew) | 88.8 ± 8.67 | 452.25 ± 44.15 |

EXAMPLE 28

Transdermal Bioavailability of MDL 73,745 from a prototype transdermal delivery system in Beagle Dogs A 'lead' prototype formulation was then evaluted in an in vivo dog model. A constant, steady state plasma level and inhibition of plasma cholineesterase activity was achieved throughout the period of patch application (96 hours). The rate of in vivo transdermal delivery in the dog was calculated to be 7.7 µg/cm²/hr.

STUDY DESIGN

Three male Beagle dogs were studied. Animals were fasted 12 h before drug administration but had free access to drinking water. The following single doses of [$^{14}$C]-MDL 73,745 were administered: intravenous (iv): 1 and 2 mg/kg; oral (po): 10 mg/kg; subcutaneous (sc): 10 mg/kg. There was a two week wash-out period between each administration. Drug was administered as a suspension in 0.5% methyl cellulose.

In a pilot study (n=1) drug was administered in a topical dermal cream (dc) formulation. This consisted of the drug mixed with Nivea® hydrating cream. Doses of 10 mg/kg and 50 mg/kg dc were applied to the shaved lateral skin.

TABLE 3

Pharmacokinetic parameters calculated from plasma concentration-time data of MDL 73745 after intravenous administration of [$^{14}$C]-MDL 73,745 (2 mg/kg)

| Dog No. | t½ (h) | Cl$_{tot}$ (ml/min/kg) | aV$_d$ (l/kg) | Metabolic Index (AUC$_{on}$/AUC$_{RAD}$) |
|---|---|---|---|---|
| 17 | 18.6 | 78.3 | 125.0 | 0.011 |
| 18 | 28.1 | 63.3 | 153.0 | 0.015 |
| 19 | 26.2 | 100.0 | 228.1 | 0.009 |
| Mean ± SD | 24.3 ± 5.0 | 80.5 ± 18.5 | 168.7 ± 53.3 | 0.012 ± 0.003 |

TABLE 4

Pharmacokinetic parameters calculated from plasma concentration-time data of MDL 73,745 after oral administration of [$^{14}$C]-MDL 73,745 (10 mg/kg)

| Dog No. | c$_{max}$ (ng/ml) | tmax (h) | t½ (h) | F* (AUC$_{po}$/AUC$_{iv}$) | Metabolic Index (AUC$_{on}$/AUC$_{RAD}$) |
|---|---|---|---|---|---|
| 17 | 15.84 | 1 | 21.4 | 0.034 | 0.0006 |
| 18 | 15.35 | 0.17 | 29.5 | 0.026 | 0.0011 |
| 19 | 21.78 | 1 | 17.4 | 0.045 | 0.0006 |
| Mean ± SD | 17.66 ± 3.58 | 0.72 ± 0.48 | 22.8 ± 6.2 | 0.035 ± 0.010 | 0.0008 ± 0.0003 |

Cl$_{tot}$ and aV$_d$ corrected for F
*normalized to the dose of 2 mg/kg iv

TABLE 5

Pharmacokinetic parameters calculated from plasma concentration-time data of MDL 73,745 after subcutaneous administration of [$^{14}$C]-MDL 73,745 (10 mg/kg)

| Dog No. | c$_{max}$ (ng/ml) | tmax (h) | t½ (h) | F* | Metabolic Index (AUC$_{on}$/AUC$_{RAD}$) |
|---|---|---|---|---|---|
| 17 | 68.4 | 6 | 12.8 | 0.41 | 0.006 |
| 18 | 42.9 | 8 | 32.7 | 0.25 | 0.007 |
| 19 | 44.7 | 4 | 24.5 | 0.36 | 0.004 |
| Mean ± SD | 52 ± 14.2 | 6 ± 2 | 23.3 ± 10.0 | 0.34 ± 0.08 | 0.006 ± 0.002 |

Cl$_{tot}$ and aV$_d$ corrected for F
*normalized to the dose of 2 mg/kg iv

DETAILS OF PATCH

MDL 73,745: 70% W/W

Adhesive Solids: 28% W/W (DuroTak 80-1074)

Loading-5 mg MDL 73,745/cm² patch

From the equation: S.ko=Cl.Css
where:
S=area (cm²) of the patch

Cl=drug clearance=960 ml/min (iv data)
$C_{ss}$=steady-state concentration (ng/ml)
ko-rate of release from the delivery system per unit surface area can be calculated:

ko=7.7 µg/hr/cm$^2$

This was the same for both doses.

TABLE 6

Mean bioavailability (F) of MDL 73,745 in dog*

| Route of administration | Dose (mg/kg) | F (%) |
|---|---|---|
| oral | 10 | 4 |
| subcutaneous | 10 | 34 |
| topical dermal cream | 10 | 7 |
| topical dermal cream | 50 | 3 |
| dermal patch | 10 | 16 |
| dermal patch | 50 | 12 |

*normalized to the dose of 2 mg/kg iv

It is now established that Alzheimer's disease and other senile degenerative diseases are characterized by a selective loss in the cerebral cortex of choline acetyltransferase, the enzyme responsible for the biosynthesis of acetylcholine. There also exists a good correlation between memory impairment or dementia and the decrement in cholinergic transmission. Thus, impaired cholinergic transmission in the central nervous system may be, at least in part, responsible for the symptomatology of Alzheimer's disease and senile dementia. In support to these conclusions such compounds as physostigmine and 1,2,3,4-tetrahydro-9-aminoacridine (THA), compounds which prevent the catabolism of acetylcholine have found a place in the treatment of Alzheimer's and other senile degenerative diseases. Indeed, it has been recognized that the extent of improvement of cognitive functions has been closely related to the degree of inhibition of acetylcholinesterase.

The acetyl cholinesterase receptor has been found to be associated with other serious disease states including the neuromuscular disorders myasthenia gravis and muscular dystrophy and glaucoma. J. Massey, et al., "The Effect of Cholinesterase Inhibitors of SFEMG in Myasthenia Gravis," *Muscle Nerve*, February 1989, 12(2), p. 154-5; W. Grogan "Treatment of Myasthenia Gravis with Pyridostigmine," *Arch. Neurol.*, October 1987, 44(10), p. 995-6; N. Kavtaradze, et al., "Course of Duchenne Muscular Dystrophy and its Treatment," Zh. Nevropatol Psikhiatr., 1986, 86(11), p. 1638-41; A. Bunke and L.Bito, "Gradual Increase in the Sensitivity of Extraocular Muscles to Acetylcholine During Topical Treatment of Rabbit Eyes with Isoflurophate," *Am. J Ophthamol.*, August 1981, 92(2), p. 259-67. The use of the compounds of formula 1 in the treatment of myasthenia gravis, muscular dystrophy and other related neuromuscular disorders as well as in the treatment of glaucoma is contemplated.

The compounds of Formula I are pharmacologically active agents capable of inhibiting acetylcholinesterase as demonstrable in standard biological in vitro and in vivo test procedures. Indeed, based upon standard laboratory procedures, it is to be shown that the compounds of Formula I are potent and selective, quasi irreversible inhibitors of acetylcholinesterase capable of demonstrating advantages over the prior art, particularly physostigmine, in their use in the treatment of Alzheimer's disease and senile dementia. The compounds, in general, will exert their acetylcholinesterase inhibitory properties within the dose range of about 0.01 mg to 5 mg per kilogram of body weight for the preferred compounds.

The ability of the compounds of this invention to produce pharmacologic activity and have therapeutic usefulness in the treatment of myasthenia gravis, muscular dystrophy, and glaucoma can be determined in standard animal models. For example, the ability of the compounds of formula 1 to produce useful pharmacologic effects in patients suffering from myasthenia gravis can be determined by the procedures of W. Nastuk, et al., "Myasthenia in Frogs Immunized against Cholinergic-Receptor Protein," *Amer. J. Physiol.,* January 1979, 236(1), p. C53-7 and S. Satyamurti, et al., "Blockade of Acetylcholine Receptors: A Model of Myasthenia Gravis," *Science*, Mar. 14, 1975, 187(4180), p. 955-7. A model for muscular dystrophy is described in M. Laskowski and W. Dettbarn, "The Pharmacology of Experimental Myopothies," *Annual Review Pharmacol. Toxicol.*, 1977, 17, p. 387-409 and a model for glaucoma is described in J. Lauber, "Three Avian Eye Enlargement Protocols as Myopia Models: Effects of Pharmacological Intervention," *J. Ocul. Pharmacol (USA)*, 1991, 711(65-76).

For pharmacological end-use applications, the compounds of Formula I are preferentially administered in the form of their pharmaceutically acceptable acid addition salts. Of course, the effective dosage of the compounds will vary according to the individual potency of each compound employed, the severity and nature of the disease being treated and the particular subject being treated. In general, effective results can be achieved by administering a compound at a dosage of about 0.01 mg to about 20 mg per kilogram of body weight per day, administered systemically. Therapy should be initiated at lower dosages. The dosage thereafter may be administered orally in solid dosage forms, e.g., capsules, tablets, or powders, or in liquid forms, e.g., solutions or suspensions. The compounds may also be injected parenterally in the form of sterile solutions or suspensions.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the formula I compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula I compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethylene glycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula I compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

As is true for most classes of compounds suitable for use as therapeutic agents, certain subgeneric groups and certain specific compounds are preferred. In this instance those compounds wherein $R_1$, $R_2$ and $R_3$ are all methyl or ethyl or mixtures thereof are preferred, and wherein one of $R_1$, $R_2$ and $R_3$ is a long-chain (8 to 10 carbon atoms) alkyl. Preferred compounds are those wherein X is F, or hydrogen, or alkyl, or $COR_9$ wherein $R_9$ is alkyl, or $CO_2R_5$ wherein $R_5$ is H or alkyl, or $CONHR_5$ wherein $R_5$ is H or alkyl. Preferred groups of compounds are also those wherein m is one and n is zero; n is one and m is zero or when both are zero. It is preferred that Y be hydrogen, alkoxy or $SiR_1R_2R_3$ with the preferred $SiR_1R_2R_3$ moieties being as described for the $SiR_1R_2R_3$ at the 3-position of depicted Formula I, although when any specific compound is a bis-$SiR_1R_2R_3$ both moieties need not be identified.

Specifically preferred compounds are those charted below as follows:

| 3-position $SiR_1R_2R_3$ | m | n | X | (Y) |
|---|---|---|---|---|
| 1. $CH_3$, $CH_3$, $CH_3$ | 0 | 0 | F | H |
| 2. $CH_3$, Et, Et | 0 | 0 | F | H |
| 3. Et, Et, Et | 0 | 0 | F | H |
| 4. Et, Et, $CH_3$ | 0 | 0 | F | H |
| 5. $CH_3$, $CH_3$, Et | 0 | 0 | F | H |
| 6. $CH_3$, $CH_3$, $CH_3$ | 0 | 0 | F | 5-$SiCH_3CH_3CH_3$ |
| 7. octyl, $CH_3$, $CH_3$ | 0 | 0 | F | H |
| 8. $CH_3$, $CH_3$, $CH_3$ | 1 | 0 | F | H |
| 9. $CH_3$, $CH_3$, $CH_3$ | 0 | 1 | F | H |

-continued

| 3-position $SiR_1R_2R_3$ | m | n | X | (Y) |
|---|---|---|---|---|
| 10. $CH_3$, $CH_3$, $CH_3$ | 0 | 0 | H | H |
| 11. $CH_3$, $CH_3$, $CH_3$ | 0 | 0 | $CH_3$ | H |
| 12. $CH_3$, $CH_3$, $CH_3$ | 0 | 0 | —$COCH_3$ | H |
| 13. $CH_3$, $CH_3$, $CH_3$ | 0 | 0 | —$COOCH_3$ | H |
| 14. $CH_3$, $CH_3$, $CH_3$ | 0 | 0 | —$CONHCH_3$ | H |

We claim:

1. A compound of the formula

I wherein Z is —C(O)C(O)R', —C(O)$CF_2CF_3$, or —$(CH_2)_n$—Q—$CF_2$X, each of m and n is zero or one with the proviso that the sum of m and n is less than two, Q is $$-\underset{\underset{O}{\|}}{C}-, \quad -\underset{\underset{OH}{|}}{CH} \quad or \quad -\underset{\underset{O-\underset{\underset{O}{\|}}{C}-R}{|}}{CH}$$

with R being H or $C_{1-10}$ alkyl

X is X' or X" with

X' being H, Br, Cl, F or $R_4$ and

X" being $COR_9$, $CO_2R_5$, $CONHR_5$ or $COR_6$, $R_1$, $R_2$, $R_3$ and $R_4$ each being $C_{1-10}$ alkyl, or $(CH_2)_p$ aryl, with p being zero, one or two, R' or $R_5$ are each H, $C_{1-10}$ alkyl, phenyl, benzyl or phenethyl, $R_9$ is $C_{1-10}$ alkyl, phenyl, benzyl or phenethyl, $R_6$ is $(NHCHR_7C(O))_qR_8$ with $R_7$ being the residue of any natural occurring α-amino acid, q is one to four and $R_8$ is $OR_5$ or $NHR_5$, Y is H, OH, ($C_{1-6}$) alkyl, ($C_{1-6}$) alkoxy, hydroxy ($C_{1-6}$) alkyl, amino($C_{1-6}$) alkyl, $NH_2$, azido, CN, $CO_2R_5$, $COR_9$, —$SO_3H$, Br, Cl, F or —$(CH_2)_xSiR_1R_2R_3$ with x being zero, one or two, or a pharmaceutically acceptable salt thereof.

2. A compound of claim 1 wherein Q is $$-\underset{|}{\overset{|}{C}}=O.$$

3. A compound of claim 1 wherein Q is $$\underset{|}{\overset{|}{C}}HOH.$$

4. A compound of claim 1 wherein Q is $$\underset{|}{\overset{|}{H}}COC(O)R.$$

5. A compound of claim 2 wherein X is X'.
6. A compound of claim 2 wherein X is X".
7. A compound of claim 2 wherein each of m and n is zero.
8. A compound of claim 2 wherein m is one.
9. A compound of claim 2 wherein n is one.
10. A compound of claim 5 wherein X' is F.
11. A compound of claim 1 wherein at least each of $R_1$ and $R_2$ are methyl or ethyl and $R_3$ is methyl, ethyl or octyl.
12. The specific compounds of claim 2 as defined in the following chart:

| 3-position $SiR_1R_2R_3$ | m | n | X | (Y) |
|---|---|---|---|---|
| $CH_3$, $CH_3$, $CH_3$ | 0 | 0 | F | H |
| $CH_3$, Et, Et | 0 | 0 | F | H |
| Et, Et, Et | 0 | 0 | F | H |
| Et, Et, $CH_3$ | 0 | 0 | F | H |
| $CH_3$, $CH_3$, Et | 0 | 0 | F | H |
| $CH_3$, $CH_3$, $CH_3$ | 0 | 0 | F | 5-$SiCH_3CH_3CH_3$ |
| octyl, $CH_3$, $CH_3$ | 0 | 0 | F | H |
| $CH_3$, $CH_3$, $CH_3$ | 1 | 0 | F | H |
| $CH_3$, $CH_3$, $CH_3$ | 0 | 1 | F | H |
| $CH_3$, $CH_3$, $CH_3$ | 0 | 0 | H | H |
| $CH_3$, $CH_3$, $CH_3$ | 0 | 0 | $CH_3$ | H |
| $CH_3$, $CH_3$, $CH_3$ | 0 | 0 | —$COCH_3$ | H |
| $CH_3$, $CH_3$, $CH_3$ | 0 | 0 | —$COOCH_3$ | H |
| $CH_3$, $CH_3$, $CH_3$ | 0 | 0 | —$CONHCH_3$ | H | wherein Et is ethyl and $CH_3$ is methyl.

13. A compound of claim 1 wherein Z is —C(O)C(O)R'.
14. A compound of claim 13 wherein Y is H and m=0.
15. A compound of claim 14 wherein R', $R_1$, $R_2$, and $R_3$ are each a methyl group.
16. A compound of claim 1 wherein Z is —C(O)$CF_2CF_3$.
17. A compound of claim 16 wherein Y is H and m=0.
18. A compound of claim 17 wherein $R_1$, $R_2$, and $R_3$ are each a methyl group.
19. A pharmaceutical composition comprising a compound of claim 1 and pharmaceutical carriers.
20. A pharmaceutical composition in unit dosage form suitable for topical administration comprising a compound of claim 1 and a suitable transdermal device.
21. A method of inhibiting acetylcholinesterase in a patient in need thereof which comprises administering to the patient an effective amount of a compound of claim 1.

* * * * *